(12) United States Patent
Reed et al.

(10) Patent No.: US 6,896,849 B2
(45) Date of Patent: May 24, 2005

(54) MANUALLY-OPERABLE MULTI-WELL MICROFILTRATION APPARATUS AND METHOD

(75) Inventors: Mark T. Reed, Menlo Park, CA (US); Jon Hoshizaki, Cupertino, CA (US)

(73) Assignee: Applera Corporation, Foster City, CA (US)

( * ) Notice: Subject to any disclaimer, the term of this patent is extended or adjusted under 35 U.S.C. 154(b) by 295 days.

(21) Appl. No.: 10/104,335

(22) Filed: Mar. 22, 2002

(65) Prior Publication Data

US 2002/0150505 A1 Oct. 17, 2002

Related U.S. Application Data

(63) Continuation-in-part of application No. 09/552,301, filed on Apr. 18, 2000, now Pat. No. 6,419,827, which is a continuation-in-part of application No. 09/182,946, filed on Oct. 29, 1998, now Pat. No. 6,159,368.

(51) Int. Cl.[7] ................................................ B01L 3/00
(52) U.S. Cl. ................. 422/99; 422/101; 210/321.75; 221/1; 221/123; 221/154; 141/130; 141/134; 141/135; 414/409
(58) Field of Search ........................... 422/99, 101, 63, 422/65, 64, 100, 103, 104; 210/321.75; 141/130, 129, 134, 135; 414/409, 939; 221/121, 123, 154; 435/287.3, 288.4, 288.3, 288.5

(56) References Cited

U.S. PATENT DOCUMENTS

| | | | |
|---|---|---|---|
| 3,463,322 A | 8/1969 | Gerarde | 210/455 |
| 3,721,364 A | 3/1973 | Lukaschewitz et al. | 220/41 |
| 4,167,875 A | 9/1979 | Meakin | 73/421 R |
| 4,246,339 A | 1/1981 | Cole et al. | 435/7 |
| 4,279,342 A | 7/1981 | Van Pelt | 206/542 |

(Continued)

FOREIGN PATENT DOCUMENTS

| | | |
|---|---|---|
| DE | 40 22 792 A1 | 2/1992 |
| DE | 297 22 473 U1 | 4/1998 |
| DE | 196 52 327 A1 | 6/1998 |
| EP | 0 131 934 B1 | 1/1985 |
| EP | 0 359 249 A2 | 3/1990 |
| EP | 0 502 371 B1 | 9/1992 |
| EP | 0 645 187 A2 | 3/1995 |
| EP | 0 676 643 A2 | 10/1995 |
| EP | 0 903 176 A2 | 3/1999 |
| EP | 0 925 828 A1 | 6/1999 |
| GB | 2 246 081 A | 1/1992 |
| WO | WO 86/07606 | 12/1986 |
| WO | WO 94/28111 | 12/1994 |
| WO | WO 95/30139 | 11/1995 |
| WO | WO 98/10853 | 3/1998 |
| WO | WO 00/25922 | 5/2000 |

OTHER PUBLICATIONS

"GENESIS Robotic Microplate Processor," *TECAN*. Document No. 390981, pp. 1–8. Ver. Nov. 1997.

(Continued)

*Primary Examiner*—Ana Fortuna
(74) *Attorney, Agent, or Firm*—Kilyk & Bowersox, P.L.L.C.

(57) ABSTRACT

A multi-well microfiltration apparatus and method are provided and feature a manual touch-off system for transferring pendent drops hanging from discharge-conduits of a discharge-conduit array to respective receiving wells or receiving holes of a corresponding receiving array, with minimum or no cross-contamination between the discharge conduits, or the receiving wells or receiving holes. The manual touch-off is achieved by manually shifting a carriage that supports one of the arrays, into a position whereat pendent drops of fluid hanging from the distal ends of the discharge conduits contact the inner sidewalls of the corresponding receiving wells or receiving holes of the receiving array.

39 Claims, 26 Drawing Sheets

U.S. PATENT DOCUMENTS

| | | | |
|---|---|---|---|
| 4,304,865 A | 12/1981 | O'Brien et al. | 435/240 |
| 4,422,151 A | 12/1983 | Gilson | 364/496 |
| 4,734,192 A | 3/1988 | Champion et al. | 210/335 |
| D297,602 S | 9/1988 | Schnur | D7/76 |
| 4,902,481 A | 2/1990 | Clark et al. | 422/101 |
| 4,927,604 A | 5/1990 | Mathus et al. | 422/101 |
| 4,948,442 A | 8/1990 | Manns | 156/73.1 |
| 4,948,564 A | 8/1990 | Root et al. | 422/101 |
| 4,969,306 A | 11/1990 | Wallin | 53/329 |
| 5,002,889 A | 3/1991 | Klein | 435/284 |
| 5,047,215 A | 9/1991 | Manns | 422/101 |
| 5,108,703 A | 4/1992 | Pfost et al. | 422/65 |
| 5,108,704 A | 4/1992 | Bowers et al. | 422/70 |
| 5,110,556 A | 5/1992 | Lyman et al. | 422/101 |
| 5,114,681 A | 5/1992 | Bertoncini et al. | 422/111 |
| 5,116,496 A | 5/1992 | Scott | 210/232 |
| 5,141,719 A | 8/1992 | Fernwood et al. | 422/101 |
| 5,201,348 A | 4/1993 | Lurz | 141/130 |
| 5,208,161 A | 5/1993 | Saunders et al. | 435/286 |
| 5,227,137 A | 7/1993 | Monti et al. | 422/101 |
| 5,264,184 A | 11/1993 | Aysta et al. | 422/101 |
| 5,282,543 A | 2/1994 | Picozza et al. | 220/255 |
| 5,283,039 A | 2/1994 | Aysta | 422/104 |
| 5,326,533 A | 7/1994 | Lee et al. | 422/101 |
| 5,342,581 A | 8/1994 | Sanadi | 422/101 |
| 5,352,086 A | 10/1994 | Mank | 414/797 |
| 5,368,729 A | 11/1994 | Stefkovich et al. | 210/266 |
| 5,380,437 A | 1/1995 | Bertoncini | 210/416.1 |
| 5,384,024 A | 1/1995 | Moring et al. | 204/299 R |
| 5,401,637 A | 3/1995 | Pocock | 435/7.1 |
| 5,409,832 A | 4/1995 | Pocock | 435/287 |
| 5,427,265 A | 6/1995 | Cautereels et al. | 220/318 |
| 5,459,300 A | 10/1995 | Kasman | 219/433 |
| 5,464,541 A | 11/1995 | Aysta et al. | 210/767 |
| 5,475,610 A | 12/1995 | Atwood et al. | 364/500 |
| 5,506,343 A * | 4/1996 | Kufe | 530/387.7 |
| 5,516,490 A | 5/1996 | Sanadi | 422/101 |
| 5,582,665 A | 12/1996 | Eigen et al. | 156/69 |
| 5,602,756 A | 2/1997 | Atwood et al. | 364/500 |
| 5,604,130 A | 2/1997 | Warner et al. | 435/286.7 |
| 5,620,663 A | 4/1997 | Aysta et al. | 422/104 |
| 5,650,323 A | 7/1997 | Root | 435/284.1 |
| 5,665,247 A | 9/1997 | Valus et al. | 210/767 |
| 5,679,310 A | 10/1997 | Manns | 422/102 |
| 5,681,492 A | 10/1997 | Van Praet | 219/400 |
| 5,710,381 A | 1/1998 | Atwood et al. | 73/864.91 |
| 5,721,136 A | 2/1998 | Finney et al. | 435/287.2 |
| 5,736,105 A | 4/1998 | Astle | 422/100 |
| 5,736,106 A | 4/1998 | Ishiguro et al. | 422/131 |
| 5,741,463 A | 4/1998 | Sanadi | 422/101 |
| 5,792,425 A | 8/1998 | Clark et al. | 422/101 |
| 5,792,430 A | 8/1998 | Hamper | 422/131 |
| 5,846,493 A | 12/1998 | Bankier et al. | 422/101 |
| 6,159,368 A * | 12/2000 | Moring et al. | 210/321.75 |
| 6,251,343 B1 | 6/2001 | Dubrow et al. | 422/102 |
| 6,338,802 B1 * | 1/2002 | Bodner et al. | 210/650 |
| 6,419,827 B1 * | 7/2002 | Sandell et al. | 210/321.75 |

OTHER PUBLICATIONS

The GENESIS Series of RSPs, *TECAN*. Document No. 390696, pp. 1–8, Ver. Oct. 1997.

"mRNA Isolation Using EVENT," *BIONEWS*. 01:3 (1996).

"Multiscreen® Assay System," *Multiscreen® Assay Systems, Rev. C. Updated: Apr. 13, 1998*. Publication P17479 Revision C. Internet Address: http//millispider.millipore.com/analytical/manuals/p17479a.htm, 1–4.

Newell, J.A. and Horton, H.L. (eds.), "Overload, Tripping, and Stop Mechanisms," *Ingenious Mechanisms*, Industrial Press Inc., New York, 109–111 (1967).

QIAGEN Product Guide. 16, 37–38 (1997).

Ruppert, A. et al., *A Filtration Method for Plasmid Isolation Using Microtiter Filter Plates, Analytical Biochemistry*. 230:130–134 (1995).

*Technical Data on Ultra–Pure QM–A Quartz Filters*, Whatman, Data Sheet No. 860 QM–AA (1992).

*Whatman Ultra–Pure QM–A Filters*, Whatman, Data Sheet No. 860 QM–AA (1992).

Product Information Sheet, Proportion–Air, Inc., Document No. SUQ100–A, (Aug. 1997).

\* cited by examiner

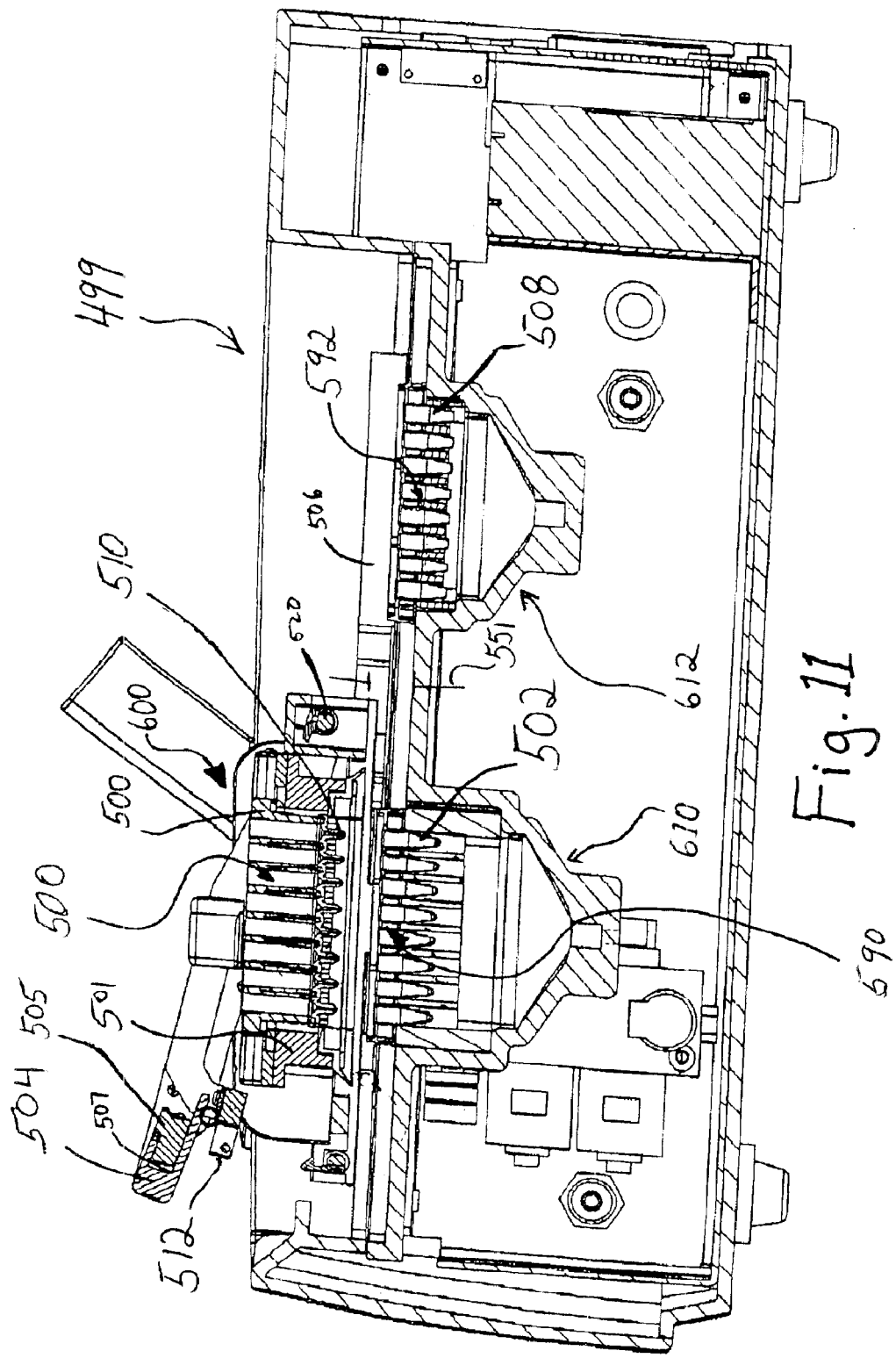

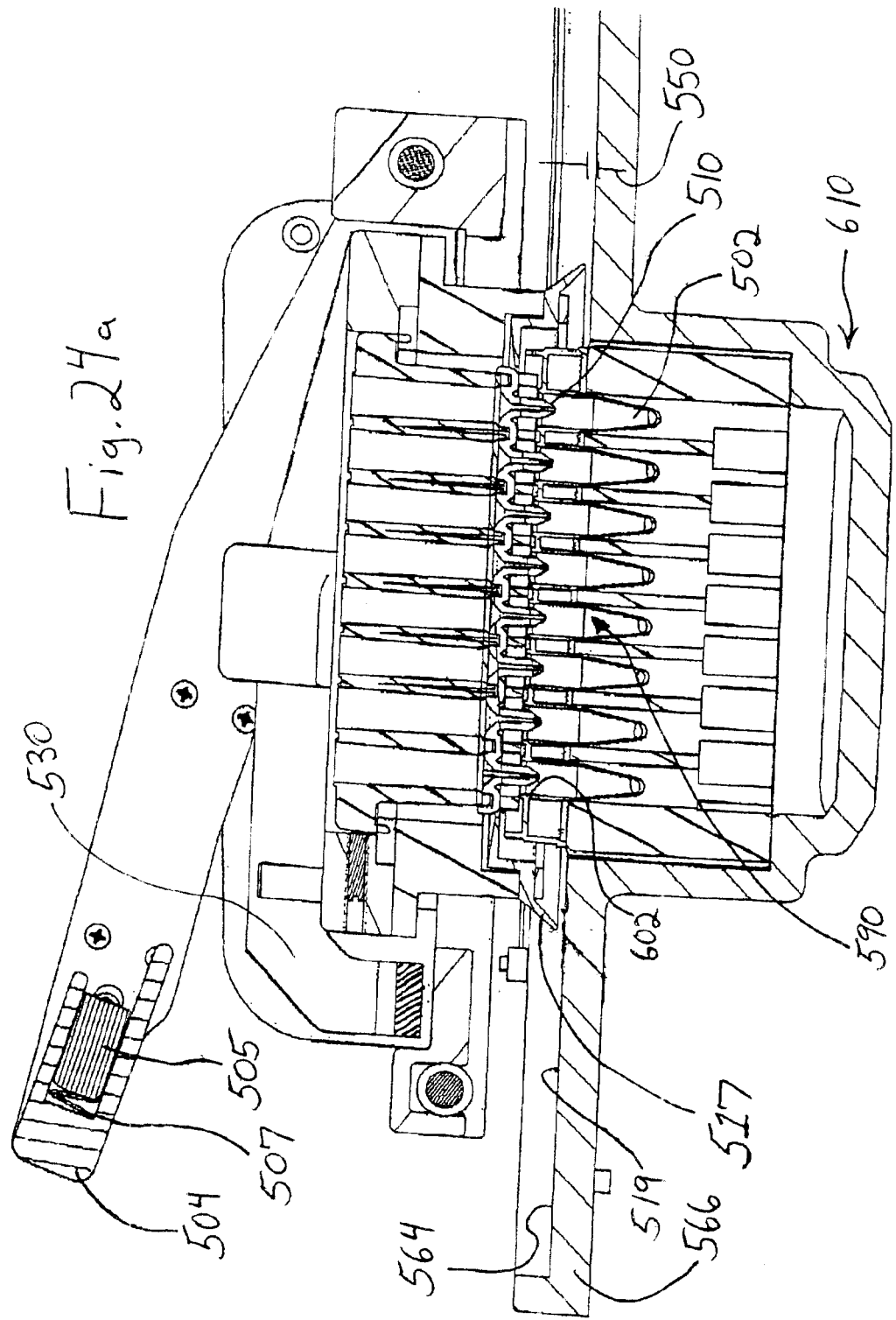

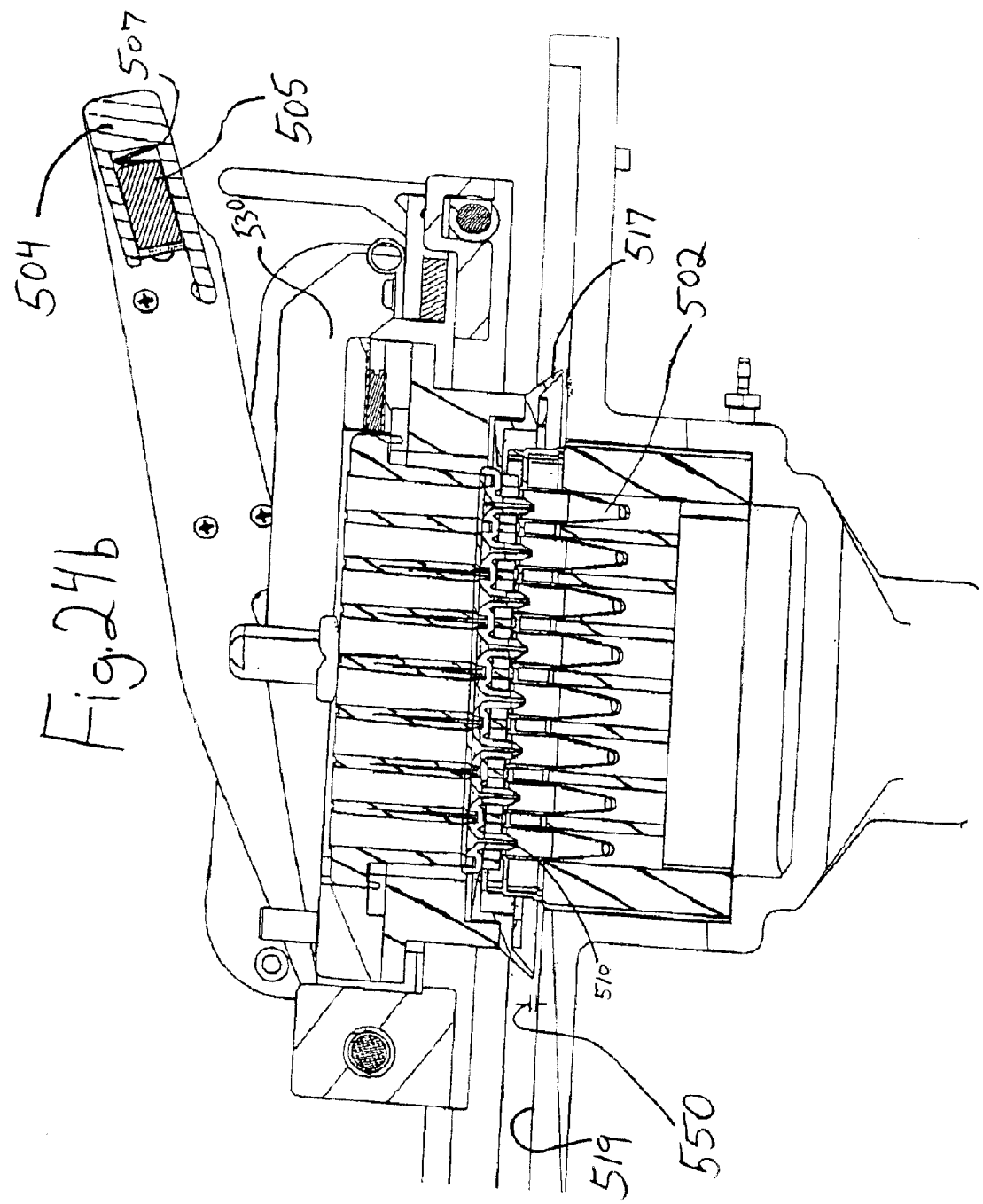

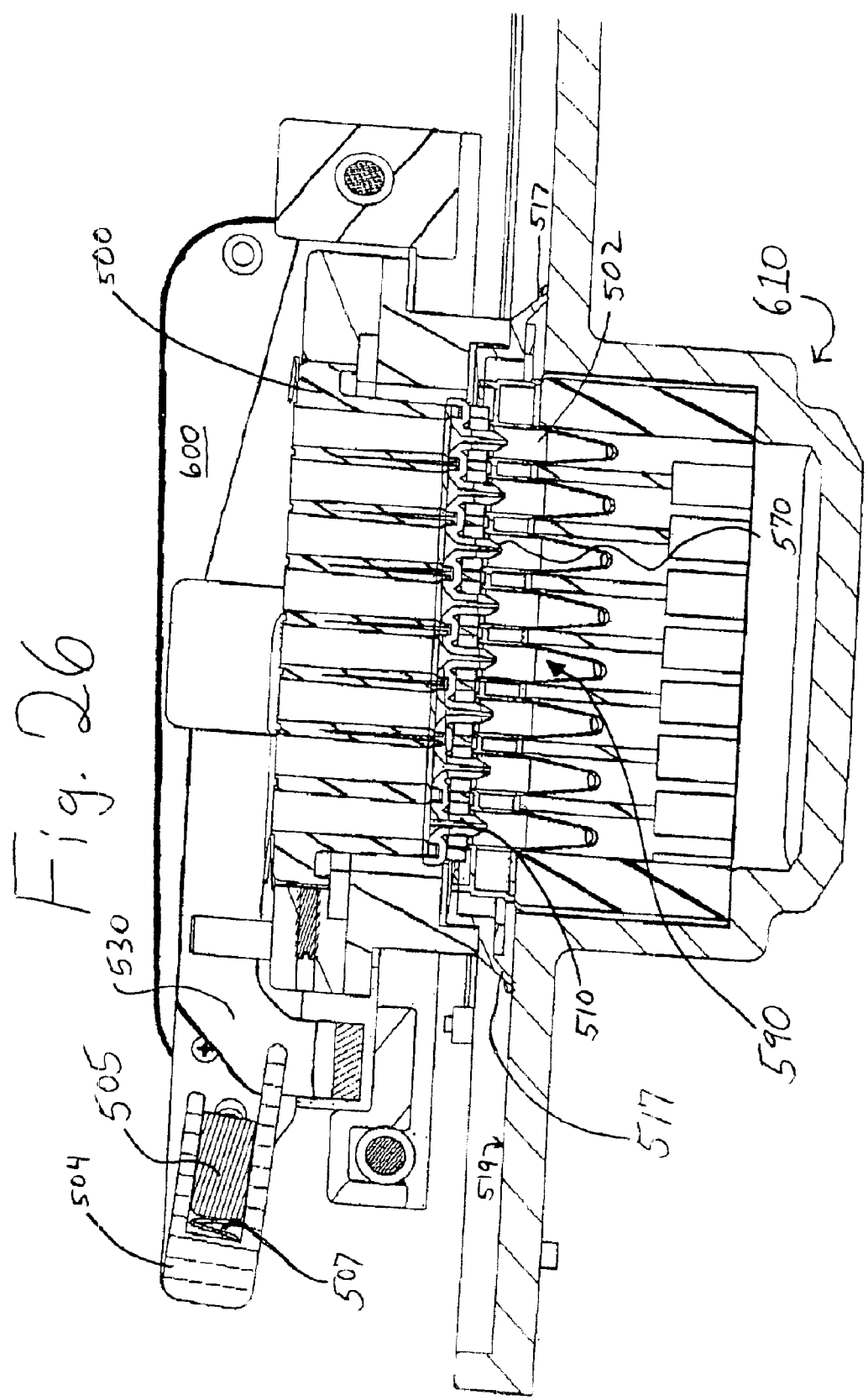

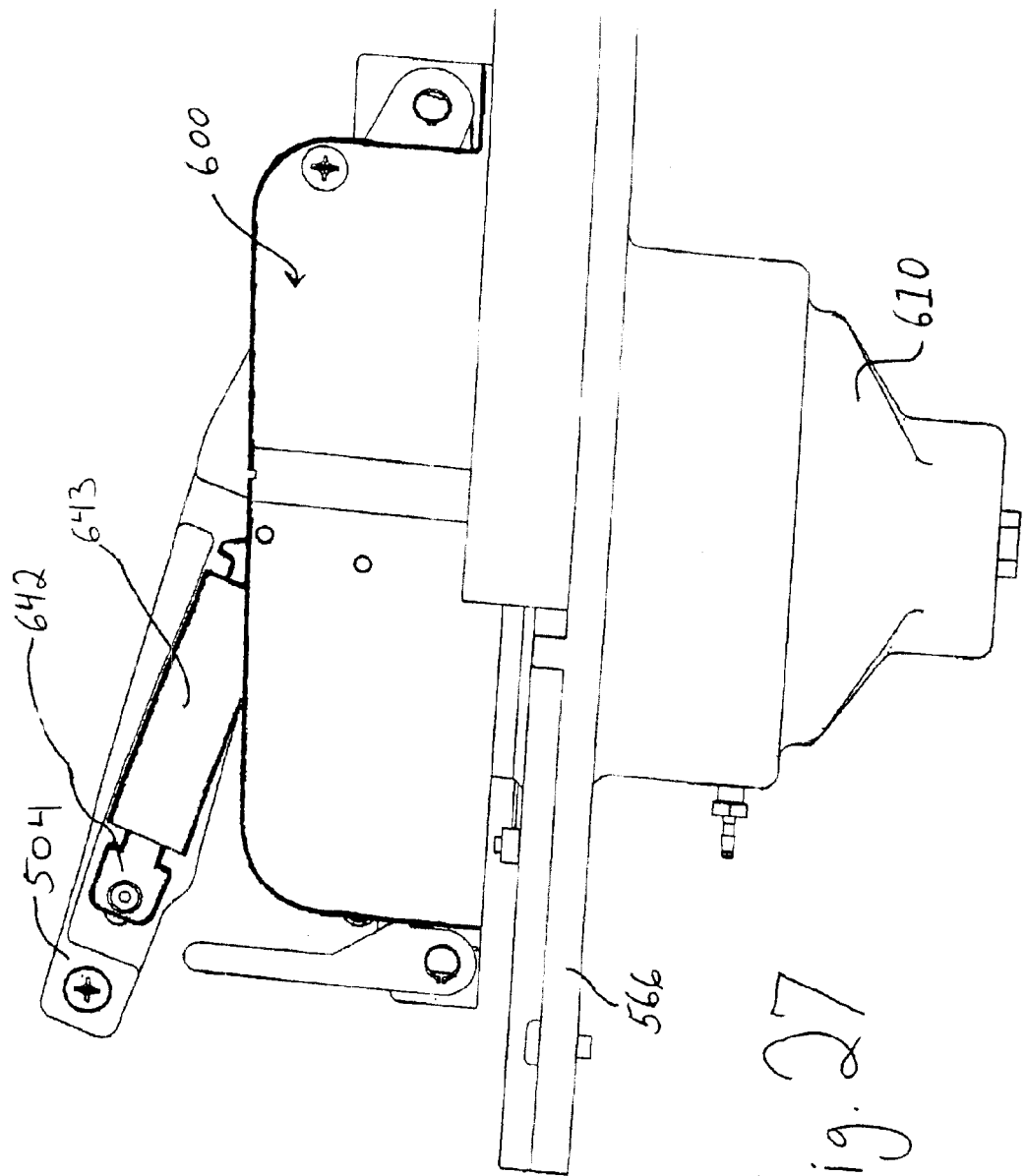

MANUALLY-OPERABLE MULTI-WELL MICROFILTRATION APPARATUS AND METHOD

This application is a Continuation-In-Part of U.S. application Ser. No. 09/552,301, filed Apr. 18, 2000 now U.S. Pat. No. 6,419,827, which in-turn is a Continuation-In-Part of U.S. application Ser. No. 09/182,946, filed Oct. 29, 1998, now U.S. Pat. No. 6,159,368, issued Dec. 12, 2000, both applications and the Patent being incorporated herein in their entireties by reference.

FIELD OF THE INVENTION

The present invention relates to multi-well microfiltration apparatus and methods for processing a plurality of fluid samples simultaneously. The present invention also relates to devices and methods for minimizing cross-contamination in such apparatus and methods.

BACKGROUND

In recent years, microtitration wells have assumed an important role in many biological and biochemical applications, such as sample preparation, genome sequencing, and drug discovery programs. A variety of multi-well arrangements, constructed according to standardized formats, are now popular.

There is a need for a multi-well microfiltration apparatus and method that provides for the separate collection of filtrate from each well of an array of wells and addresses problems associated with cross-contamination caused by aerosol formation and/or pendent drops.

The present invention addresses this need and provides a multi-well microfiltration apparatus and method that minimizes or avoids cross-contamination during processing a plurality of liquid samples simultaneously.

SUMMARY

Various embodiments of the present invention provide a microfiltration apparatus with a manual touching-off device for processing a plurality of liquid samples in a multi-well array while reducing or avoiding cross-contamination between the multiple wells. Various embodiments of the present invention provide a method for processing a plurality of liquid samples simultaneously with a multi-well microfiltration apparatus, wherein the method minimizes or avoids cross-contamination between the multiple wells.

According to various embodiments of the present invention, an apparatus is provided for avoiding cross-contamination due to pendent drops of fluid hanging from a plurality of discharge conduits corresponding to the wells. The plurality of discharge conduits can be disposed, for example, in a discharged-conduit array, and can be positioned above a corresponding receiving array of receiving wells or receiving holes. The apparatus can include a carriage configured to carry one of the arrays relative to the other. For example, the carriage can carry the discharge-conduit array. The carriage is adapted for movement along a path. The path can be, for example, a first, generally horizontal, axis. The carriage can be adapted for movement from a neutral position whereat the discharge-conduit array and the corresponding receiving array are substantially axially aligned. The apparatus can also include a vertical positioning assembly supporting one of the arrays, for example, the discharge-conduit array for movement of the array along a second path, for example, a generally vertical axis. The second path can include, for example, an elevated position, a lowered position, and an intermediate touch-off position.

According to various embodiments of the present invention, cross-contamination caused by pendent drops is avoided or minimized by first positioning the discharge-conduit array at the touch-off position. At the touch-off position, pendent drops of sample hanging from the discharge conduits of the discharge-conduit array come into contact with respective inner sidewalls of respective receiving wells or receiving holes of a corresponding receiving array. The contact between the pendent drops and the inner sidewalls can be achieved, for example, by reciprocal movement of one of the discharge-conduit array and the receiving array along a generally horizontal axis, for example, a first, generally horizontal, linear axis.

According to various embodiments of the present invention, a manually-operated handle is connected to the carriage, directly or indirectly, and to the vertical positioning assembly, directly or indirectly. Movement of the manually-operated handle can, according to various embodiments of the present invention, translate into the movement of the vertical positioning assembly along the generally vertical axis.

According to various embodiments of the present invention a system is provided wherein an apparatus of the present invention is included in an assembly for enabling movement of the apparatus from a first treatment station to a second treatment station. The assembly can include a common platform on which the first and second treatment stations can be supported, as by, for example, fixing, securing, mounting, or connecting.

According to various embodiments of the present invention, a method of avoiding or minimizing cross-contamination due to pendent-drops is provided whereby a touch-off procedure is conducted to enable pendent drops hanging from discharge conduits of an array to contact the inner sidewalls of respective receiving wells or receiving holes of a corresponding receiving array. The contact can occur in a manner to carry-away, such as by wicking, or hydrophilic action, the pendent drops hanging from the distal ends of discharge conduits. According to various embodiments of the present invention, the contact between the drops and the inner sidewalls can occur without contact between the discharge conduits themselves and the inner sidewalls, or with contact between only distal tips of the discharge conduits and the respective inner sidewalls. Multi-step methods are also provided according to various embodiments of the present invention whereby one or more touch-off procedures are carried out at two or more sample treatment stations.

According to various embodiments of the present invention, a device is provided for shifting a discharge-conduit array in two or more directions from a reference, beginning, or home position along a generally horizontally extending axis, and then returning the array back to the home position, for example, back and forth one time. The shifting device can include a manually-operated actuator for moving the array-carrying carriage, for example, without a stepper motor. In such an embodiment, the shifting can be performed by an operator moving or actuating a handle in a manner to enable control over the speed, timing, frequency, and forcefulness of the manual shifting.

The invention may be more fully understood with reference to the accompanying drawing figures and the descriptions thereof. Modifications that would be recognized by those skilled in the art are considered a part of the present invention and within the scope of the appended claims.

BRIEF DESCRIPTION OF THE DRAWINGS

The structure and manner of operation of the invention, together with the further objects and advantages thereof, may best be understood by reference to the following description taken in conjunction with the accompanying drawings, in which identical reference numerals identify identical elements in the different figures, and in which:

FIG. 11 is a cross-sectional side view in partial breakaway of a manually-operated device according to an embodiment of the present invention with the vertical positioning system and carriage in the elevated position and the handle in the beginning position;

FIG. 24a is a partial cross-sectional view of a device according to an embodiment of the present invention showing the carriage and discharge conduit array in the touch-off position and the handle in the elevated position;

FIG. 24b is a partial cross-sectional view, of the reverse side of the device shown in FIG. 24a;

FIG. 26 is a partial cross-sectional view of a device according to an embodiment of the present invention showing the carriage and discharge-conduit array in the lowered, sealed, or closed position and the handle in the set or lowered position; and FIG. 27 is a partial side view of a device according to an embodiment of the present invention showing the handle in the elevated position and the carriage in the touch-off position.

Figure 1:
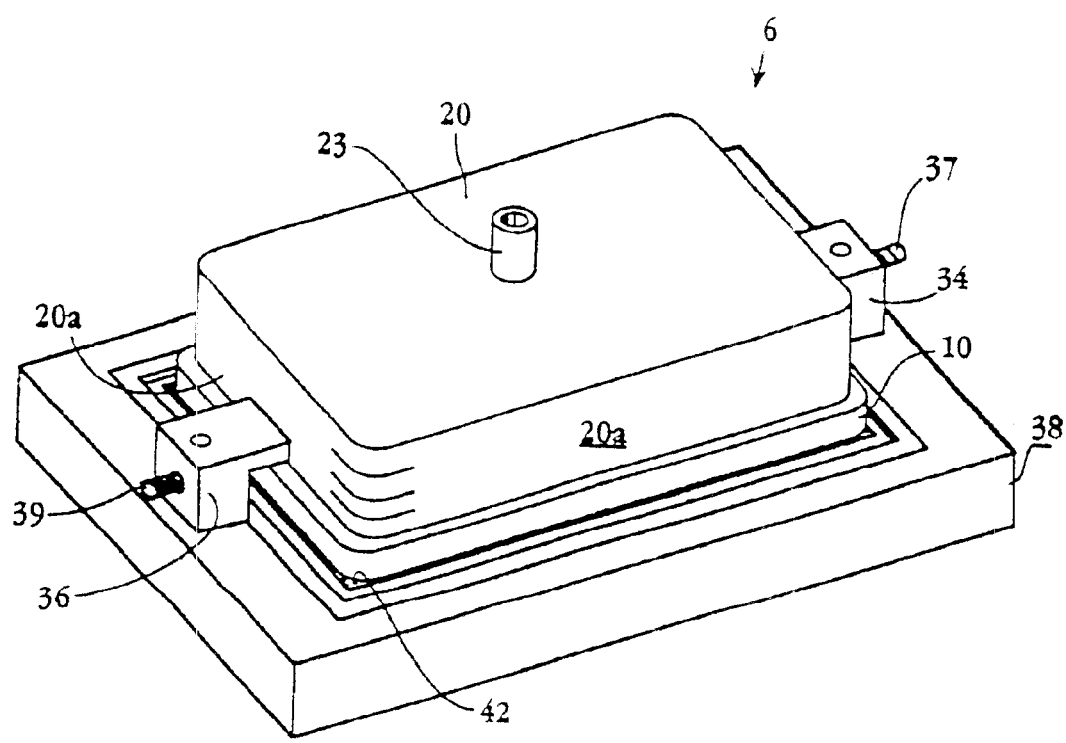
FIG. 1 is a perspective view of a multi-well microfiltration device that can be used with the apparatus and method of an embodiment of the present invention.

Other various embodiments of the present invention will be apparent to those skilled in the art from consideration of the specification and practice of the invention described herein, and the detailed description that follows. It is intended that the specification and examples be considered as exemplary only, and that the true scope and spirit of the invention includes those other various embodiments.

DETAILED DESCRIPTION OF CERTAIN EMBODIMENTS OF THE PRESENT INVENTION

Although it is to be recognized that either the discharge-conduit array or the receiving array can be vertically moved, horizontally moved, or moved along both a horizontal plane and a vertical axis, the present invention is described in detail with respect to movement of an upper discharge-conduit array. According to various embodiments of the present invention, a manually-operated apparatus is provided for avoiding cross-contamination due to pendent drops of fluid hanging from a plurality of discharge conduits disposed in a discharge-conduit array above a corresponding receiving array of receiving wells or receiving holes. According to various embodiments of the present invention, the apparatus includes a carriage configured to move the discharge-conduit array horizontally in two or more directions. The carriage can be configured to carry the discharge-conduit array linearly in a reciprocal movement in either of at least two directions along a generally horizontal axis. The carriage can carry the array from, for example, a neutral position to a touch-off position. According to various embodiments of the present invention, the carriage can carry the discharge-conduit array horizontally, for example, reciprocally horizontally, to first and second, different, touch-off positions. According to various embodiments of the present invention, the carriage can be configured to carry the discharge-conduit array in a plurality of different substantially horizontal directions into a plurality of different positions.

The shifting of the discharge-conduit array in various directions, for example, in various horizontal directions, can effect a touch-off operation whereby pendent drops of fluid hanging from the discharge conduits of the array are brought into contact with the inner sidewalls of respective receiving wells or receiving holes of a corresponding receiving array. The shifting operation can provide a mechanism whereby the hydrophilicity, or wicking, of the pendent drops of fluid enables the drops to be gently carried away from the discharge conduits without requiring a shaking action and without necessitating a contact of the discharge conduit itself with any portions of the sidewalls of the receiving wells or receiving holes. According to various embodiments of the present invention only the distal tips of the discharge conduits contact the inner sidewalls of the respective corresponding receiving wells or receiving holes.

The discharge conduit can be shifted from being axially aligned with the receiving wells or receiving holes to positions having parallel, but non-axial, orientations with respect to the corresponding receiving wells or receiving holes.

According to various embodiments of the present invention, a vertical positioning assembly is provided for supporting the discharge-conduit array for linear movement along a second, generally vertical, axis. The vertical positioning assembly can provide movement of the discharge-conduit array between, for example, an elevated position, a lowered position, and an intermediate position. The elevated position can be a position, for example, an open position whereat the discharge conduits clear the receiving wells or receiving holes of the receiving array. The lowered position can be a position, for example, a sealed position whereat the discharge conduits extend down into respective receiving wells or receiving holes of a corresponding receiving array. The intermediate position can be, for example, a touch-off position in between or intermediate to the lowered and elevated positions. The touch-off position can be a position whereat pendent drops hanging from the discharge conduits contact respective sidewalls of respective receiving wells or receiving holes of the receiving array. According to various embodiments of the present invention, methods are provided whereby movement of the discharge-conduit array while the array is vertically-positioned for touch-off results in a shifting of the discharge-conduit array from a neutral position to one or more touch-off positions. The movement of the discharge conduit array can be, for example, a linear reciprocal movement.

According to various embodiments of the present invention, a manually-operable handle can be connected to the carriage directly, or indirectly. According to various embodiments of the present invention, the manually-operable handle can be connected to the vertical positioning assembly, either directly or indirectly. The handle can be configured with respect to the carriage, with respect to the vertical positioning assembly, or with respect to both the carriage and the vertical positioning assembly, such that movement of the handle translates into the reciprocal movement of the carriage, the linear movement of the vertical positioning assembly, or both.

The handle can be configured for pivotal movement, for example, an up and down reciprocal movement, a back and forth reciprocal movement, an arcing movement, or the like, for example, from a beginning or elevated position to a set position. The handle can be configured for movement from a set, locked, or lowered position to an elevated and/or intermediate position, and if an intermediate or touch-off position is used, from there to a release or elevated position. The handle can include two interworking levers that together or separately move to achieve the beginning position of the handle, the set position of the handle, the touch-off or intermediate position of the handle, and the release or open position of the handle. The touch-off position can be the same as the elevated position.

According to various embodiments of the present invention, the beginning position of the handle can be an elevated position, the set position of the handle can be a depressed position, and if a separate touch-off position of the handle is used, it can be intermediate to, or in between, the beginning position and the set position. The release position can be the same position as the beginning position. In the release position, for example, the carriage can be configured for movement from a first treatment station to one or more additional stations, such as a second treatment station, whereby the first and second treatment stations in such an embodiment can be, for example, supported by a common platform as by mounting, fixing, securing, and/or connecting.

According to various embodiments of the present invention, a vacuum system can be provided in a system that includes an apparatus of the present invention. The vacuum system can provide a device for drawing a vacuum through the discharge-conduit array, an array of receiving holes, both arrays, and the like. The vacuum system can be configured to operate only when the carriage and discharge conduit array are in the lowered position.

According to various embodiments of the present invention, an apparatus is provided whereby the carriage is connected to the handle such that when the handle is in the elevated beginning position, the vertical positioning assembly positions the carriage and, if present, a discharge-conduit array, in the elevated position. The carriage can be connected to the handle such that when the handle is in the set position, the vertical positioning assembly positions the carriage and, if present, a discharge-conduit array, in the lowered position. The carriage can be connected to the handle such that when the handle is in the intermediate position, the vertical positioning assembly positions the carriage and, if present, a discharge-conduit array, in the touch-off position.

According to various embodiments of the present invention, when the handle is depressed into the set position, a releasable lock is activated that maintains the vertical positioning assembly in the set position. The lock maintains the set position until it is released, for example, by a manual operation such as by pressing a button. According to various embodiments of the present invention, the handle includes two levers and both levers are depressed to achieve the set position and to activate the releasable lock.

According to various embodiments of the present invention, the receiving array is positioned on or in a platform. The receiving array can be, for example, secured into place, as by being held, maintained, fixed, mounted, or in any way restricted in movement, by the platform. Systems according to various embodiments of the present invention are provided whereby such a platform further includes a second treatment station for securing a second receiving array of receiving wells or receiving holes. According to such embodiments, the platform can be configured so as to provide a position-shifting assembly for moving the carriage from the first treatment station to the second treatment station. The position-shifting assembly can include rails, tracks, guides, bumpers, or any combination of features that directs the carriage from the first treatment station to the second treatment station whereby the discharge-conduit array can be axially aligned with two different receiving arrays at different treatment stations.

According to various embodiments of the present invention, shifting or movement between the first treatment station and the second treatment station can be enabled, for example, when the vertical positioning assembly supports the discharge-conduit array in the elevated position, for example, when the handle is in the beginning position. Similar, or the same, movements of the handle at the second treatment station, as at the first treatment station, can result in a second discharge operation whereby samples from the discharge-conduit array are forced into or through the receiving wells or receiving holes of a respective second receiving array at the second treatment station.

According to various embodiments of the present invention, the first treatment station can be, for example, a sample wash station or a sample binding station. The second treatment station can be a sample collection station or a second sample wash station. Multiple operations such as washes can be carried out at the first treatment station, the second treatment station, or at both the first treatment station and the second treatment station.

According to various embodiments of the present invention, a method is provided for avoiding cross-contamination due to pendent drops of fluid hanging from a plurality of discharge conduits disposed in a discharge-conduit array above a corresponding receiving array of receiving wells or receiving holes. The methods of various embodiments of the present invention can include providing a carriage-positioning assembly that can effect movement of the carriage from a first treatment station to a second treatment station, for example, between two treatment stations on a common platform. The touch-off operation according to various embodiments of the present invention can be effected at the first treatment station, at the second treatment station, or at both the first treatment station and the second treatment station.

According to various embodiment of the present invention, a shifting means is provided for effecting the movement of the carriage horizontally along the first axis. The shifting means can include an actuator for manually moving the receiving array relative to the discharge-conduit array.

Thus, in an embodiment of a device according to the present invention, an actuator is provided that is in mechanical communication with the discharge conduit array such that manual force applied to the actuator induces horizontal, for example, linear movement of at least one of the discharge-conduit array and the receiving array.

The present invention also provides methods for reducing or avoiding cross-contamination, removing inhibitory wash solutions, and increasing the percent yield of the archiving, collection, and filtration operations of a microfiltration apparatus according to the present invention, by using the manual touch-off apparatus and methods taught herein.

Another aspect of the present invention provides a method for separately collecting filtrate from an array of microfiltration discharge-conduit wells in a corresponding array of closed-bottom receiving wells held by a receiving tray situated below the microfiltration discharge-conduit well array.

In an embodiment of the present invention, a method is provided that includes the steps of:

(A) placing one or more fluid samples in a plurality of microfiltration wells discharge conduits of a discharge-conduit array;

(B) drawing a vacuum along pathways extending from each discharge conduit downward through a plane defined by an upper surface of the receiving tray at a point at or adjacent a corresponding receiving well to a region beneath the receiving array, thereby causing a filtrate to flow from each discharge conduit and to collect or pass through the respective wells or receiving holes of the receiving array; and (C) obstructing aerosols formed from the filtrate at any one discharge conduit from moving across the upper surface of the receiving array to a non-corresponding receiving well or receiving hole of the receiving array, thereby limiting cross-contamination.

According to an embodiment of the present invention, each vacuum pathway passes through a gas-permeable matrix disposed in a cavity between the discharge-conduit array and the receiving array. The gas-permeable matrix can be comprised of a porous hydrophilic polymer material, such as ethyl vinyl acetate (EVA) or the like. In an exemplary arrangement, the gas-permeable matrix circumscribes the region between each discharge conduit and a corresponding receiving well or receiving hole.

According to yet another embodiment of the present invention, the vacuum pathways pass through the plane of the receiving array upper surface by way of vents that traverse the receiving array proximate each of the receiving wells or receiving holes of the receiving array. The gas-permeable matrix can also cover the vents.

In yet other various embodiments of the present invention, each of the vacuum pathways extends from one or more respective microfiltration well discharge conduit into a respective receiving well or receiving hole prior to passing through the vents.

According to various embodiments of the present invention, a receiving array is used that has receiving holes, for example, open-bottom wells, wherein the vacuum pathways pass through the plane of the receiving array upper surface and then down and out of the open bottoms of the wells.

The receiving wells or receiving holes can include, according to various embodiments of the present invention, a first plate having a plurality of columns and a second plate having a plurality of discharge conduits. Each column of the first plate can have a first inner bore defining a lumen within the column, and an end region for receiving a filter medium within the column. The end region can define a second inner bore having a diameter greater than that of the first inner bore, and a transition region that joins the second inner bore to the first inner bore. A filter medium for filtering sample can be positioned within each column end region, adjacent the transition region. Each discharge conduit can have an upstanding upper end region aligned with and received within a corresponding column end region so as to form a substantially fluid-tight interface therebetween. The discharge conduit upper end region has a terminal rim region for supporting a circumferential region of the filter medium such that each filter medium is held between a column transition region and the terminal rim region of a corresponding discharge conduit.

After the fluid sample is filtered through the filter and passed into the sample well as described, pendent drops of liquid sample can remain fixed to the surface of the distal tips of the discharge conduits, that is, to the "drip directors" openings. It is desirable to remove such pendent drops from the tips of the drip directors so that they leave the tips and are received by the receiving well or receiving hole. The operation according to various embodiments of the present invention, for effecting such a transfer is referred to herein as a "touch-off" of or "touching-off" the pendent drops.

In a touching-off method according to various embodiments of the present invention, the discharge-conduit array is moved in opposite horizontal directions to touch opposite surfaces of the same respective corresponding receiving well or receiving hole. The provision of the sample well chamfered surface promotes more thorough touching-off of the pendent drops with minimum or no contact required between the discharge conduits and the inner sidewalls. Because the receiving well chamfer is angled to match the angle of the discharge conduit chamfer, the pendent drops hanging from the drip directors are provoked to be pulled toward inner sidewalls of the receiving wells. The touching-off operation can be useful in minimizing or avoiding cross contamination caused by dripping of liquid sample into a non-aligned receiving well during removal of the receiving array.

In further embodiments of the present invention, a vacuum system is provided for drawing adherent drops of fluid hanging from the discharge conduits in a direction away from the receiving wells and up into the discharge conduits.

According to yet further various embodiments of the present invention, a method is provided that includes:

(i) touching-off, in a substantially simultaneous fashion, pendent drops of fluid hanging from discharge conduits of a discharge-conduit array to inner sidewalls of respective receiving wells or receiving holes of a corresponding receiving array; and (ii) drawing adherent drops of fluid hanging from the discharge conduits in a direction away from the respective receiving wells or receiving holes of the corresponding receiving array, and up into the discharge conduits.

According to various embodiments of the present invention, a vacuum chamber is provided that communicates with the discharge-conduit array from a side thereof opposite the receiving array. Evacuation of the vacuum chamber is effective to urge pendent drops of fluid hanging from the discharge conduits in a direction away from the receiving wells or receiving holes of the receiving array and into the discharge conduits.

According to various embodiments of the present invention, an apparatus is provided that can include:

(i) a carriage configured to carry a discharge conduit array having a plurality of discharge conduits with distal ends, the carriage being adapted for linear reciprocal movement in either of two directions along a first, generally horizontal, axis from and to a neutral position whereat the discharge-conduit array and the receiving array are substantially axially aligned;

(ii) an actuator or handle for manually moving the carriage and thus the discharge-conduit array and the receiving array relative to each other a given distance from the neutral position in one of the two directions depending upon the direction of manual force applied to the carriage such that pendent drops of fluid hanging from the distal ends of the discharge conduits are simultaneously touched-off to inner sidewalls of respective receiving wells or receiving holes of the corresponding receiving array, and, optionally, (ii) a compression spring connected to the actuator or handle in a manner permitting the spring (a) to provide a predetermined amount of resistance to movement of the actuator or handle from the neutral position, and (b) to compensate for or absorb some of any linear overshoot due to excess manual effort beyond the amount required to manually move or shift the carriage and discharge conduits.

According to various embodiments of the present invention, the actuator contains at least a lever, wherein the lever can rotate about an axis of rotation. According to various embodiments of the present invention, the lever can pivot about a pivot point. According to various embodiments of the present invention, a pivot point can be provided mounted on or connected to a device, and the device can further include a receiving array, and may further include a recess or opening for holding the receiving array. The actuator can further include or be made of a handle, for example, a two-part handle having two lever arms.

According to various embodiments of the present invention, the carriage is configured to carry the discharge-conduit array, while the receiving array remains stationary. A vertical positioning assembly can be disposed on or in conjunction with the carriage to support the discharge-conduit array for movement such as linear movement along a second, generally vertical, axis between a lowered position whereat the discharge conduits extend down into respective receiving wells or receiving holes, and an elevated position whereat the discharge conduits clear the receiving wells.

According to various embodiments of the present invention, the carriage is configured to carry the receiving array while the discharge conduit array remains stationary. A vertical positioning assembly can be disposed on or in conjunction with the carriage to support the receiving array for movement such as linear movement along a second, generally vertical, axis between an elevated position whereat the discharge conduits extend down into respective receiving wells or receiving holes, and a lowered position whereat the discharge conduits clear the receiving wells or receiving holes.

According to various embodiments of the present invention, a horizontal carriage and vertical positioning assembly system is provided that enables horizontal movement of a first array in a first direction and horizontal movement of a second array in a second direction that differs from the first direction. The first array can be a discharge-conduit array and the second array can be a receiving array, or vice versa.

Still a further embodiment of the present invention provides a method for avoiding cross-contamination due to pendent drops of fluid hanging from a plurality of discharge conduits disposed in an array above a corresponding array of closed-bottom receiving wells or receiving holes. According to various embodiments of the present invention, the method includes:

(i) touching-off, in a substantially simultaneous fashion, pendent drops of fluid hanging from the discharge conduits to inner sidewalls of respective receiving wells; and (ii) drawing pendent drops of fluid hanging from the discharge conduits in a direction away from the corresponding receiving array and into the discharge conduits.

The touching-off step can be carried out by shifting the discharge-conduit array or the receiving array, along a plane that is substantially orthogonal to the longitudinal axes of the receiving wells, while the receiving wells are maintained in a substantially fixed position. Each of the discharge conduits can be shifted into contact with inner sidewall portions of respective receiving wells, and can then be shifted into contact with laterally opposing inner sidewall portions of the same respective receiving wells.

Another embodiment of the present invention provides an actuator for manually moving at least one of the discharge-conduit array and the receiving array relative to the other. The actuator can include a handle and/or lever in mechanical communication with the discharge-conduit array, for example, through a carriage, such that manual force applied to the handle or a part thereof, results in movement of the discharge-conduit array in a generally horizontal direction. In this way, the application of a manual force to the handle causes the discharge-conduit array to shift. The distal ends of the discharge conduits can be shifted so that hanging pendent drops make contact with sidewall portions of respective receiving wells or receiving holes of the receiving array. Then, by the application of a different manual force to the actuator, the discharge-conduit array can be shifted so that the hanging drops of fluid contact laterally opposing sidewall portions of the respective receiving wells or receiving holes. The touching-off can be achieved according to the present invention when the discharge-conduit array is in, for example, an archiving, collection, or filtration position such as shown as station "a" in FIG. 11, or in, for example, a wash or waste collection position such as shown as station "b" in FIG. 11.

The step of drawing pendent drops of fluid can be affected by establishing a reduced pressure such as by a vacuum, above the discharge conduits.

Further various embodiments of the present invention are described and illustrated herein, and will become obvious with reference to the following more detailed description of those various embodiments. The embodiments of the present invention described herein are only exemplary illustrations thereof. The following detailed description of various embodiments of the present invention is also exemplary in nature.

Figure 2:
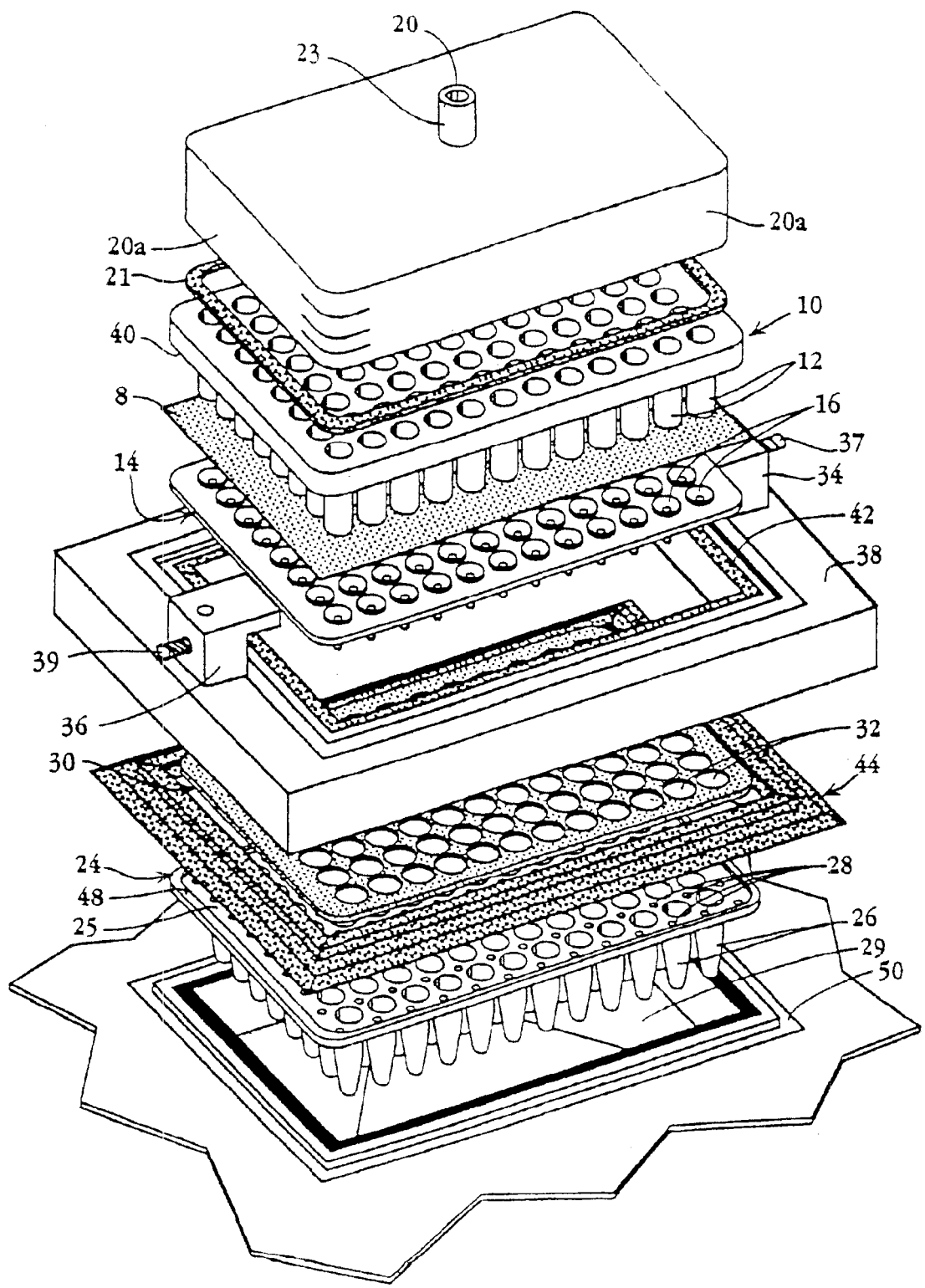
FIG. 2 is an exploded view of the multi-well microfiltration device of FIG. 1.
Figure 3:
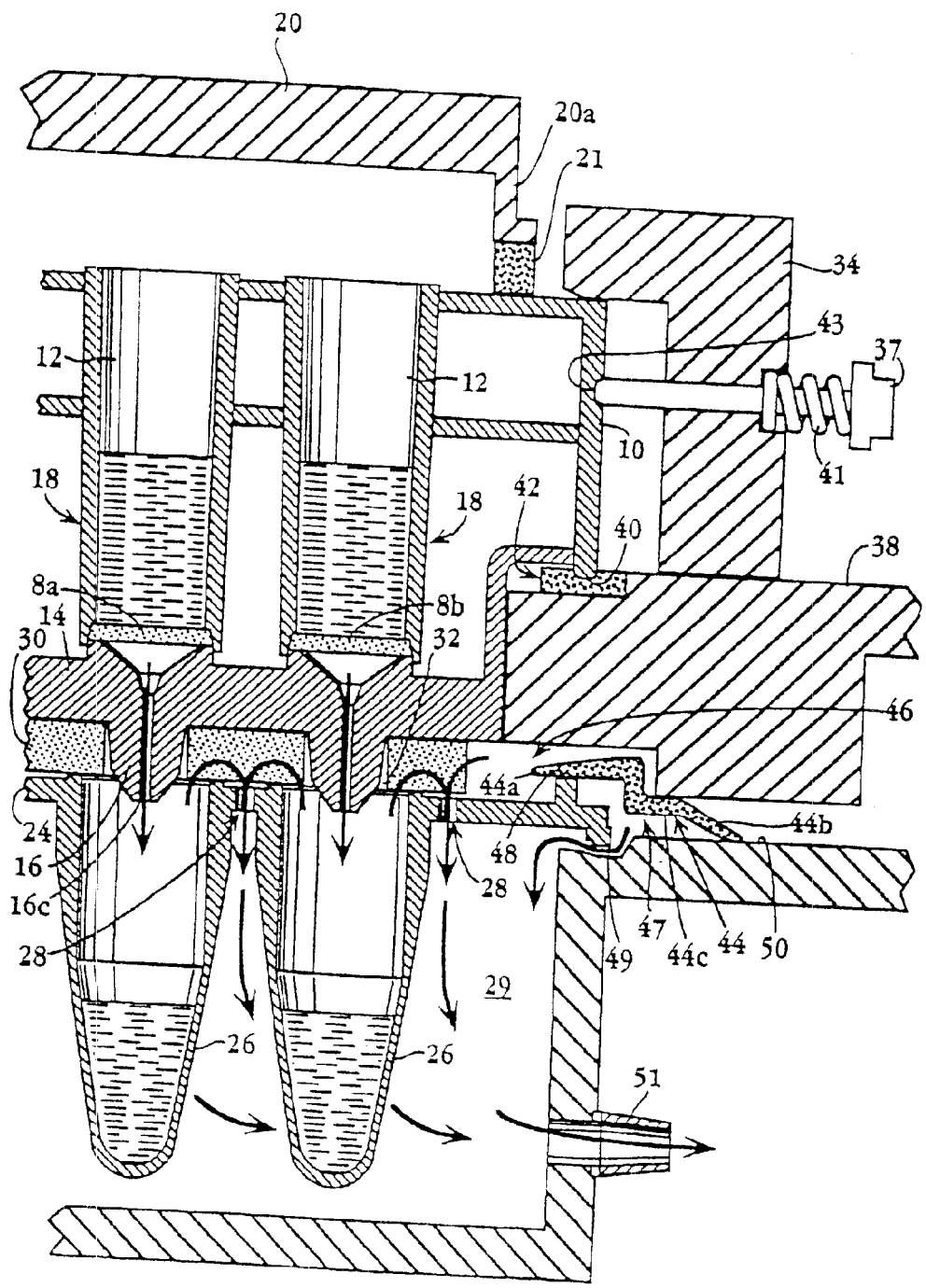
FIG. 3 is a partial cross-sectional side view of the multi-well microfiltration device of FIGS. 1 and 2.

FIGS. 1–3 show, in perspective, exploded and partial side-sectional views, respectively, an embodiment of a multi-well microfiltration apparatus constructed in accordance with various embodiments of the present invention. Even greater details about the multi-well microfiltration apparatus and systems that use the apparatus, can be found in U.S. Pat. No. 6,159,368, which is incorporated herein in its entirety by reference.

In the assembly stage of manufacture, a filter sheet or membrane, indicated in FIG. 2 by the reference numeral 8, is located between a column tray, or plate, 10 having an array of open-bottom mini-columns, such as 12, and a drip-director tray, or plate, 14 having an array of drip directors, such as 16, corresponding to the mini-columns. Upon registering and mating mini-columns 12 with drip directors 16, a discharge-conduit array is formed in the form of a multi-well microfiltration array, denoted generally in FIG. 3 by the reference numeral 18, each mini-column having a discrete filter element or medium (e.g., a plug, disc, or the like), such as 8a and 8b, positioned therein. The inner walls of each mated mini-column/drip-director pair bound a flow pathway that extends downward through the well 18.

As shown in FIGS. 2 and 3, each microfiltration well has an interior region, or lumen, that is substantially circular in horizontal cross-section. It should be appreciated, however, that microfiltration wells of any desired geometrical cross-section (e.g., oval, square, rectangular, triangular, etc.) could be used. Similarly, the wells may be of any desired shape when viewed along their longitudinal axes, e.g., straight, tapered or other shape. In one embodiment, the walls of each well have a slight outward taper (i.e., the well diameter increases) along the direction extending from the well's upper, loading end toward the filter medium.

Greater details about the plates, filters, columns, drip directors, and other components of the illustrated embodiment, and methods of making those components, can be found in U.S. Pat. No. 6,159,368, which is incorporated herein in its entirety by reference.

With reference once again to FIGS. 1–3, an upper vacuum chamber 20 is situated above column plate 10. Upper vacuum chamber 20 is adapted for movement between (i) a mounted position, whereat four depending circumferential walls, denoted as 20a, form a substantially airtight seal with an upper, peripheral surface of column plate 10 via an interposed resilient gasket 21, and (ii) a retracted position, whereat chamber 20 is spaced apart from column plate 10. The hollow interior of chamber 20 is pneumatically connectable to an external vacuum source via a hosecock 23 extending through the top of chamber 20. A reduced pressure can be established above the sample wells by bringing chamber 20 to its mounted position atop column plate 10 and then evacuating chamber 20.

In some situations, it may be desirable to establish an increased pressure above the sample wells (e.g., to facilitate the flow of samples through the filter media and out of the wells via the lower discharge conduits). In such cases, chamber 20 can be pressurized by way of a suitable pressure source (e.g., a pump).

A receiving array in the form of a receiving plate or receiving plate 24 is located below drip director plate 14. Receiving plate 24 includes an upper planar surface, denoted as 25, and an array of closed-bottom wells, such as 26, depending therefrom. The receiving-well array corresponds to the drip-director array, permitting the separate collection of filtrate from each sample well. The receiving plate is adapted to fit inside an open reservoir of a lower vacuum chamber, denoted as 29, with the receiving wells or receiving holes extending down into the reservoir.

Apertures or vents, such as 28, extend through the upper planar surface 25 of receiving plate 24. For reasons that will become apparent, at least one aperture should be located adjacent each receiving well. The apertures 28 permit fluid communication between the regions above and below the plate 24. By this construction, a vacuum drawn from beneath the receiving plate will extend to the regions above the plate and inside the wells.

Although not shown in the figures, the present invention also provides a plate like receiving plate 24, except having open-bottom wells as opposed to the closed-bottom wells of plate 24. Otherwise, the plate of open-bottom wells is configured like receiving plate 24. That is, the plate of open-bottom wells provides structure for effectively carrying out filtrations and/or washings, while avoiding cross-contamination. However, instead of separately collecting filtrate in the various wells, the filtrate passes through the wells and out of the open bottoms. It is contemplated that the plate of open-bottom wells will be used in a manner like that described herein for plate 24, except that the situation will not call for the separate collection of filtrate. For example, the plate of open-bottom wells is particularly useful in performing intermediate washings. As used herein, "collection plate" and "receiving plate" are used synonymously and interchangeably, with either term referring to a plate, intended for placement beneath a drip-director array, having either open-bottom wells or closed-bottom wells, as appropriate for the task at hand. Where the separate collection of filtrate is to take place, it is understood that the wells are of a closed-bottom type. Optionally, a receiving plate having open-bottom wells may be formed without vent features (such as 28), as the vacuum can flow directly down and out through the bottom of each well.

A cross-flow restrictor (also referred to as an aerosol guard), denoted as 30, which is generally pervious to gases but substantially impervious to aerosols, is interposed between the upper surface of receiving plate 24 and the lower surface of drip-director plate 14. In the illustrated embodiment, cross-flow restrictor 30 has a plurality of passages, such as 32, arranged in an array complementing the receiving-well array and drip-director array. Passages 32 permit filtrate to pass from each drip director 16 to a corresponding receiving well 26. In the illustrated arrangement, each drip director 16 extends through a respective passage. Except for such passages, cross-flow restrictor 30 substantially fills the area between the confronting faces of the drip-director and receiving-well plates (14, 24).

Preferably, means are provided for supporting the assembled mini-column and drip-director plate arrangement, and assisting in the formation of an airtight seal between this arrangement and the lower vacuum chamber 29. In the illustrated embodiment, a rectangular carriage frame, denoted as 38, is configured to support the mini-column and drip-director plate assembly. Clamps 34, 36 are pivotally mounted about generally vertically extending axes at opposing ends of frame 38. Clamps 34, 36 are operable to engage and hold the column and drip-director assembly on frame 38, with a lower peripheral edge 40 of the column and drip-director plate assembly pressed against a gasket 42 disposed on the upper surface of frame 38 about the frame's central opening.

A spring-loaded centering pin, such as 37 and 39, may extend through each clamp 34, 36. In the embodiment of FIG. 3, centering pin 37 has a shank that is urged by a spring 41 to sit within a complementary recess or depression 43 formed in a sidewall of column plate 10. In another embodiment (not shown), three spring-loaded centering pins are employed, with two pins located at positions on a long side of the arrangement and one pin located at a position on a short side, together operable to push the tray against a corner. In this way, the components can be readily centered (on axis).

A stepped gasket, indicated generally at 44, is disposed adjacent a lower surface of frame 38 about the frame's central opening. Gasket 44 has (i) an upper, inwardly projecting flap portion, denoted as 44a, having a lower surface adapted to engage an upwardly projecting ridge 48 disposed about the periphery of receiving plate 24, and (ii) a lower flap portion, denoted as 44b, that extends diagonally downward and outward for engaging an upper surface 50 surrounding the open reservoir of lower vacuum chamber 29. A central plateau region of stepped gasket 44, denoted as 44c, is secured to frame 38 by any suitable means. For example, central plateau region 44c can be attached using an adhesive and/or fasteners. In one embodiment, gasket 44 is interposed between frame 38 and a rectangular clamping frame (not shown). In this embodiment, the rectangular clamping frame is disposed adjacent the plateau region 44c of gasket 44, on a side of gasket 44 opposite frame 38. The clamping frame is then snugly secured to frame 38 using threaded fasteners that pass through aligned passages (not shown) formed in the clamping frame and gasket, and are received in internally threaded bores extending partially into frame 38 from the frame's lower surface. Together, upper gasket 42 and lower gasket 44 assist in forming substantially airtight seals between (i) the upper microfiltration well assembly and the carriage frame, and (ii) the carriage frame and the lower vacuum chamber assembly, respectively.

The gaskets (21, 42, and 44) may be formed of any deformable, resilient, substantially inert material capable of forming a seal. Examples of such materials are silicone, rubber, polyurethane elastomer and polyvinyl chloride. The thickness of each gasket is not critical, provided only that it is sufficient to form a seal. Typical gasket thicknesses will range from about 1 mm to about 5 mm.

Once appropriate airtight seals are formed, evacuation of lower vacuum chamber 29 establishes a substantially uniform pressure drop over all of the sample wells 18, permitting a plurality of individual samples (e.g., up to ninety-six in the illustrated embodiment) to be processed simultaneously on the membrane of choice.

Those skilled in the art will recognize that the choice of filter medium will depend on the intended use of the well. Exemplary filter materials that can be used can be found, for example, in U.S. Pat. No. 6,159,368, which is incorporated herein in its entirety by reference.

In another embodiment the filter medium is a porous element that acts as a frit, serving to contain a column packing material (e.g., reversed-phase or size-exclusion packings).

Various aspects of the present invention address problems pertaining to (i) cross-contamination due to wicking across a common filter sheet and (ii) individual filter elements entrapping sample constituents within substantial dead volumes, and are discussed more fully in U.S. Pat. No. 6,159,368, which is incorporated herein in its entirety by reference.

Figure 4:
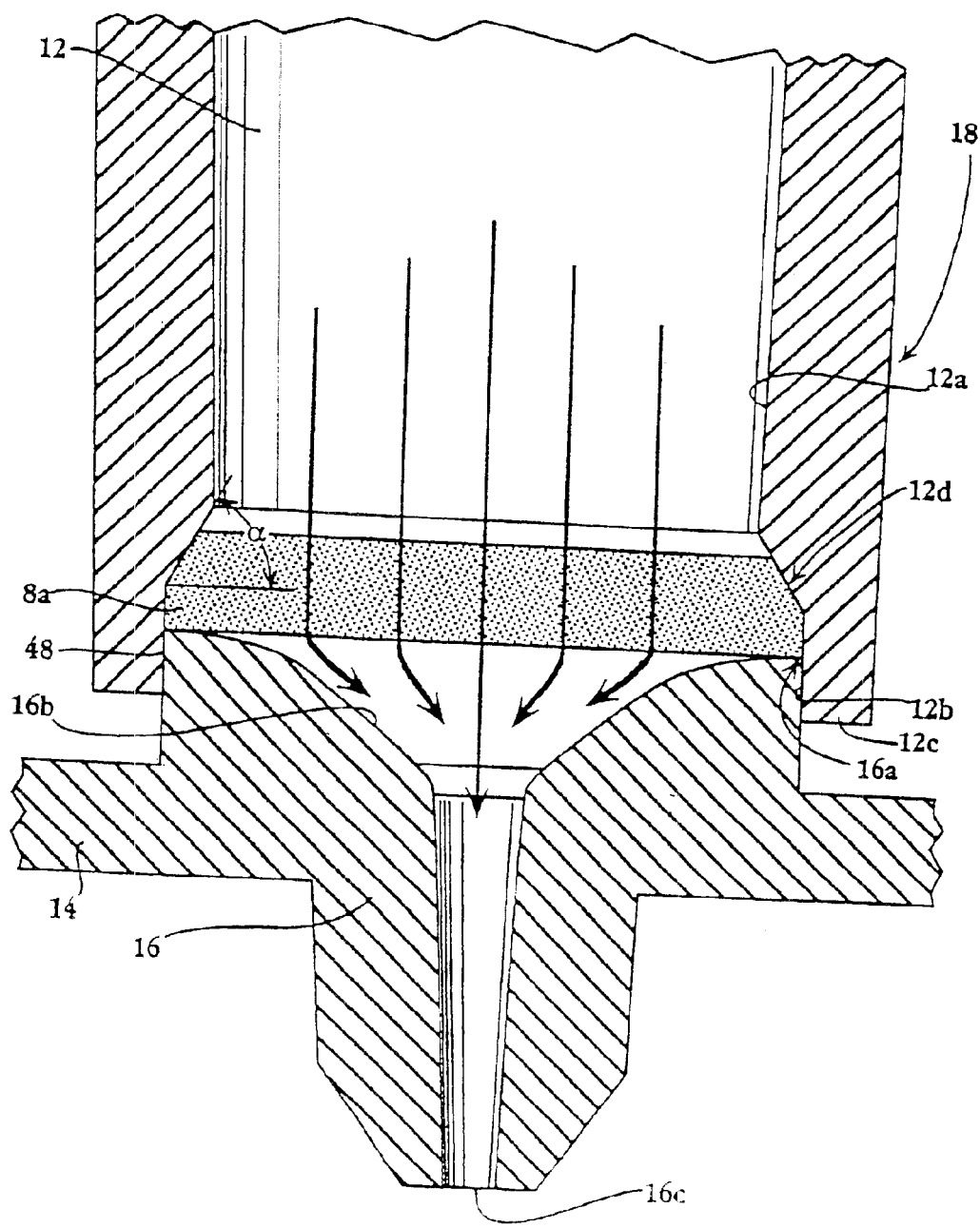
FIG. 4 shows, in enlarged detail, a microfiltration well with a discharge conduit taken from a sectional view of FIG. 3.

In the embodiment of FIG. 4, mini-column 12 is formed with a bore 12a and a counterbore 12b, the latter extending upwardly from the mini-column's lower end or lip 12c.

Between the bore 12a and counterbore 12b, lies a transition region. The transition region provides a constricted-diameter region, or shoulder, within the mini-column lumen capable of cooperating with an upper portion of a corresponding drip director to maintain the filter element in place. The junctions of the transition region with the bore and counterbore may be of any suitable shape, for example, as described in U.S. Pat. No. 6,159,368, which is incorporated herein in its entirety by reference.

According to the embodiment depicted in FIG. 4, the transition region between bore 12a and counterbore 12b defines an internal, annular shoulder, denoted as 12d. In this embodiment, each of the junctions of shoulder 12d with bore 12a and counterbore 12b defines a hard angle or corner. Between such junctions, the shoulder 12d takes the form of an annular wall having a substantially constant taper, with a decreasing circumference along the direction from counterbore 12b to bore 12a. Longitudinally, the surface of shoulder 12d is oblique to the surfaces of bore 12a and counterbore 12b. Preferably, the surface of shoulder 12d forms an acute angle with a plane perpendicular to the mini-column's central axis and extending through the junction of shoulder 12d with counterbore 12b. In one embodiment, this angle, denoted as α in FIG. 4, falls within the range of about 30–85 degrees; and is preferably within the range of about 60–85 degrees.

Drip-director 16 is configured to facilitate elution of a mobile phase from the well by funneling it toward a lower opening. In the embodiment of FIG. 4, drip director 16 includes (i) an annular edge or rim 16a disposed above the plane of the upper surface of drip-director plate 14, (ii) depending convergent sidewalls 16b, and (iii) a downspout or outlet port 16c disposed below the plane of the lower surface of drip-director plate 14. The downwardly sloping, inner surface of the convergent sidewalls 16b, between rim 16a and outlet port 16c, defines a conical and/or horn-shaped cavity at the lower region of the well lumen.

As previously mentioned, an upper portion of drip director 16 provides supporting structure adapted to abut a lower peripheral edge region of the filter element. In the embodiment of FIG. 4, such structure takes the form of upper, annular rim 16a. The surface area of the uppermost region of rim 16a (i.e., the portion of rim 16a that directly confronts, and is available to support, the lower peripheral edge region of the filter element) may vary. In one preferred embodiment, the uppermost region of rim 16a defines a narrow circular line. In this embodiment, the contact between rim 16a and filter element 8a is tangential in nature. That is, the region of contact between rim 16a and filter element 8a defines a very thin, circular line. Rim 16a contacts no more than about 15%, and preferably less than about 10%, and more preferably less than about 5% of the bottom surface area of the filter element 8a.

In the illustrated embodiment, the peripheral edge region of filter element 8a is preferably pinched or compressed between shoulder 12d and rim 16a in a manner effective to secure the filter element in place and to press its circumferential side-edge against the inner surface of the column lumen. This arrangement discourages upward or downward movement of the filter element and prevents leakage around its edges.

Figure 5:
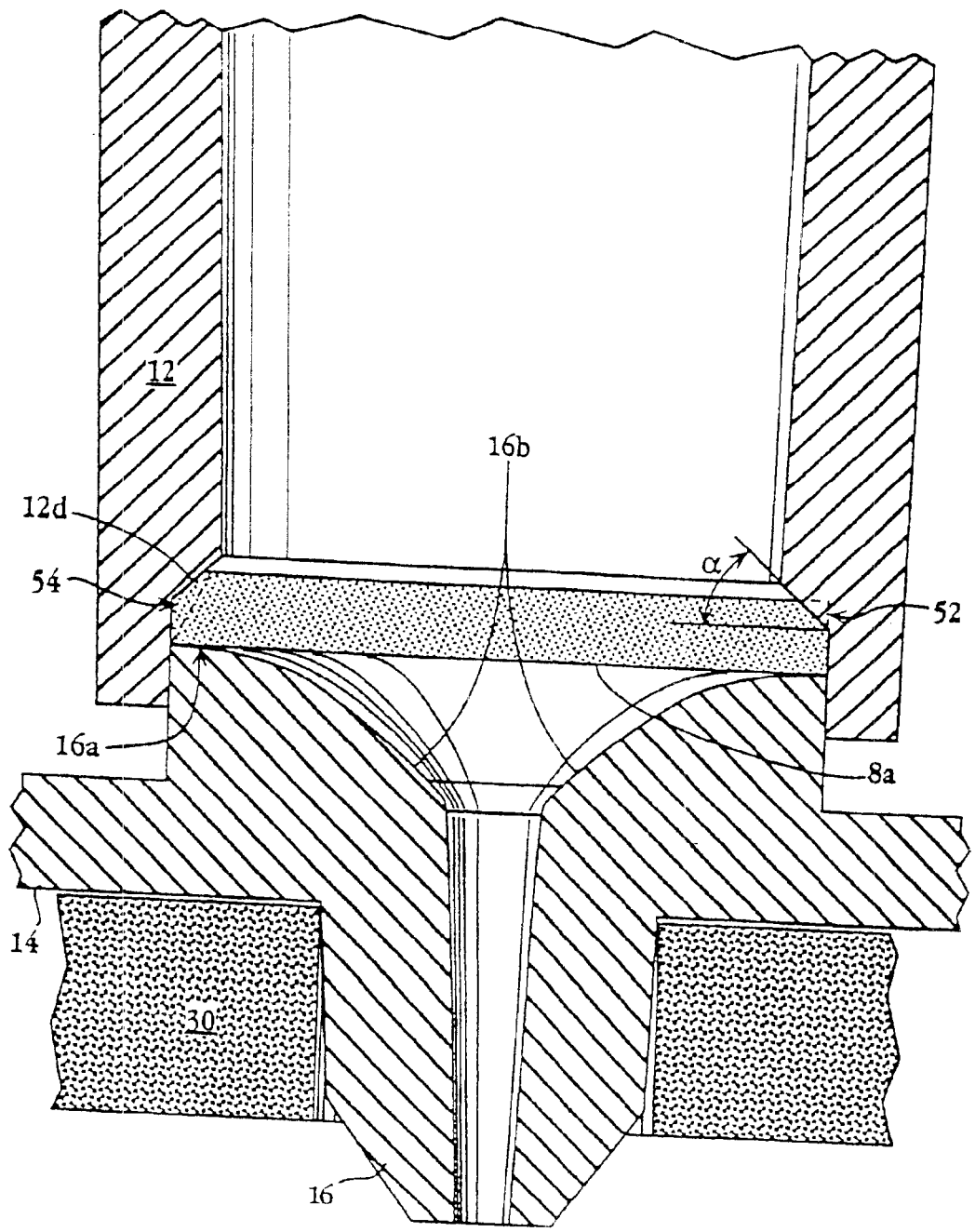
FIG. 5 is a partial cross-sectional side view showing a microfiltration well with discharge conduit and an aerosol guard useful in the apparatus and method of an embodiment of the present invention.

FIG. 5 is a partial side-sectional view showing a microfiltration well constructed in accordance with one preferred embodiment of the invention. Filter element 8a is compressed between drip-director rim 16a and mini-column shoulder 12d such that the membrane is securely held in place. Further, the compression fit causes the outer circumferential side-edge region of the filter element to press against the inner wall of the column lumen in a manner effective to avoid any bypassing of fluid around the edges of the filter element. Shoulder 12d extends into the mini-column lumen at an angle α of about 45 degrees. Further, the uppermost surface area of rim 16a is minimal, approaching that of a circular line, so that only the outermost perimeter of the filter element's lower surface is in contact therewith.

With continued reference to FIG. 5, both the compression and the dead volume have been estimated for a filter element in one such microfiltration well using the computer-aided engineering package "Pro/ENGINEER" (Release 18), by Parametric Technology Corporation (Waltham, Mass.). The membrane compression for a 950 μm thick QM-B (Whatman, Inc., Tewksbury, Mass.) filter element having a diameter of 6.88 mm is estimated to be only about 2.6 μl (area 52 in FIG. 5), and the dead volume for such a filter element is estimated to be only about 3 μl (area 54 in FIG. 5).

Beneath the filter element 8a, the inner surface of the convergent sidewalls 16b of drip director 16 define a cavity. The cavity is configured to expose the great majority of the filter element's lower surface to open, or free, space. By providing such free space below the filter element 8a (i.e., volume between the drip director's convergent sidewalls 16b and the lower surface of the filter element), preferential flow pathways are avoided.

In another embodiment, to prevent sagging or dislodgement of the filter element into the cavity, the invention provides structure for supporting central points or regions of each filter element. For example, a support buttress may be disposed within the cavity of drip director 16 to provide a resting point, edge or surface for one or more centrally located regions of the filter element's lower surface, as is described in greater detail in U.S. Pat. No. 6,159,368, which is incorporated herein in its entirety by reference.

Figure 6:
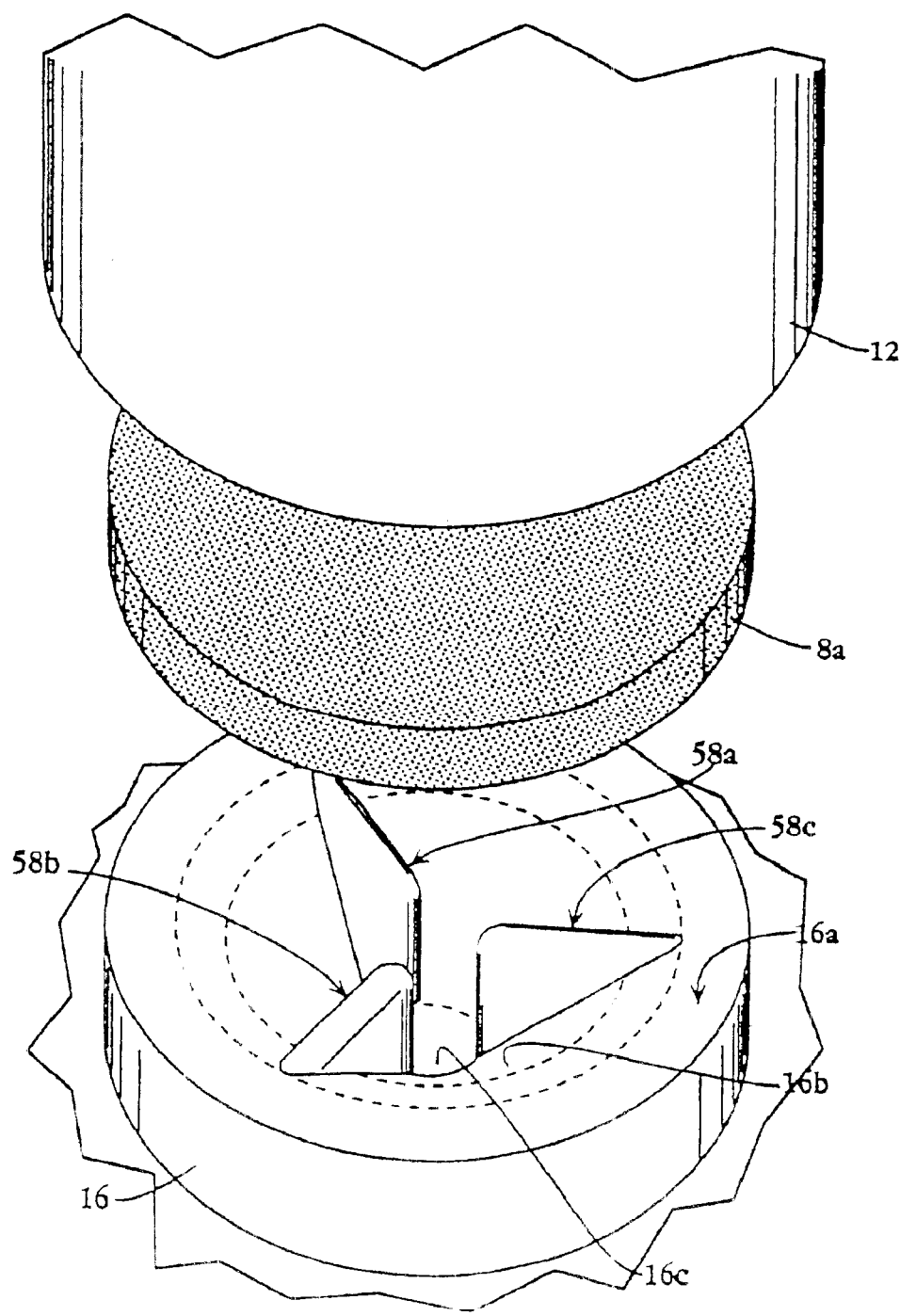
FIG. 6 is an exploded view of a microfiltration well of a discharge-conduit array showing a membrane-support structure in the form of three fin-like support buttresses.
Figure 7:
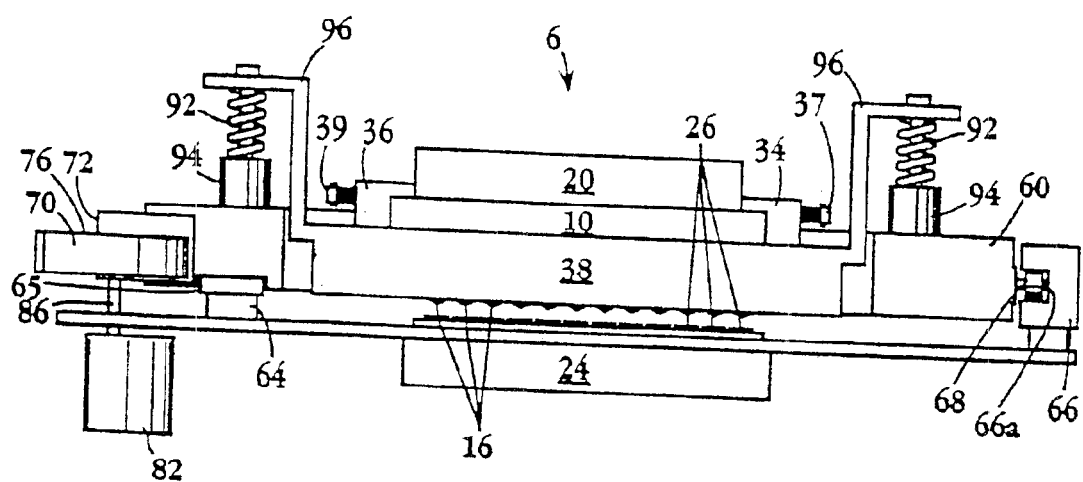
FIG. 7 is an end view from one end of a carriage assembly for effecting relative movement between the discharge conduits of a discharge-conduit array and the receiving wells or receiving holes of a receiving array, useful with the apparatus and method of an embodiment of the present invention.
Figure 8:
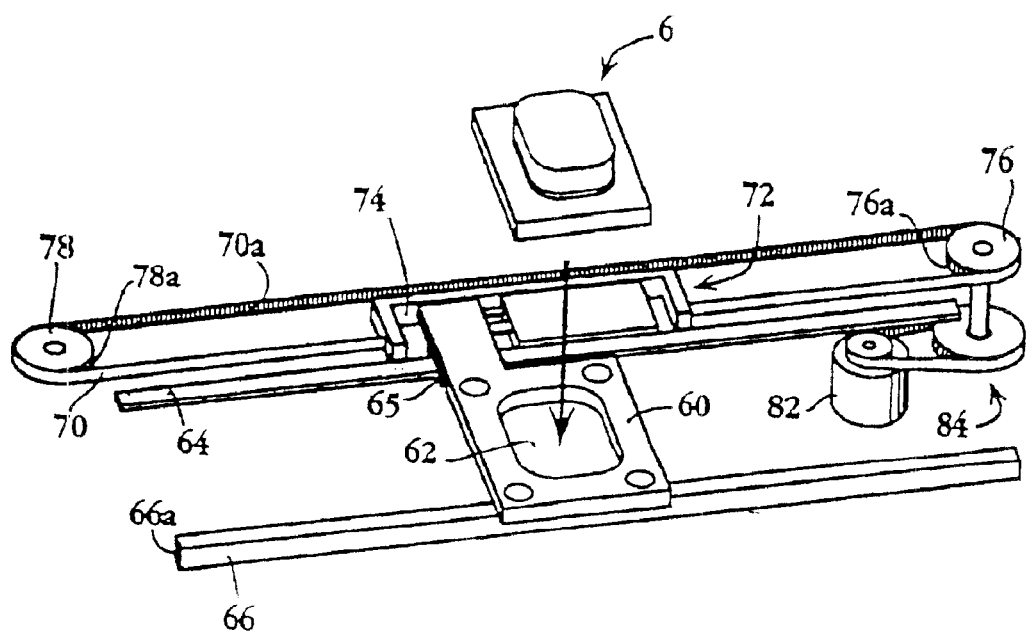
FIG. 8 is a partially exploded, perspective view showing a carriage assembly for effecting relative movement between a discharge-conduit array and a receiving array, according to an embodiment of the present invention.

In one preferred embodiment, shown in the exploded view of FIG. 6, such supportive structure takes the form of three fin-like support buttresses, denoted as 58a–58c, positioned radially and spaced equidistantly within the cavity of drip-director 16 about central outlet port 16c. It should be appreciated that any other reasonable number of support buttresses, e.g., 4 or 6, may be employed instead. Small portions of the lower surface of filter element 8a rest on top of elongated, narrow, uppermost surfaces or edges of the support buttresses 58a–58c. In the illustrated embodiment, the support buttresses 58a–58c are formed integrally with the drip director 16.

Greater details about the discharge-conduit array and methods of manufacturing the array are described in U.S. Pat. No. 6,159,368, which is incorporated herein in its entirety by reference.

A further aspect of the present invention pertains to a multi-well microfiltration arrangement that provides for the flow of filtrate out of each well, while avoiding cross-contamination due to aerosols or splattering.

As previously described, the receiving-well array corresponds to the drip-director array, with each drip director disposed directly over a receiving or collection well. The receiving-well plate, in turn, is adapted to fit within an open reservoir of a lower vacuum chamber, with the receiving wells extending down into the reservoir. Upon establishing a suitable vacuum in the lower chamber, filtrate will flow from each microfiltration well and into corresponding receiving wells. In accordance with this aspect of the invention, means are provided for discouraging filtrate-associated aerosols and residues present at any one well from traveling to, and potentially contaminating neighboring wells. Such means can include, for example, a cross-flow restrictor, also referred to as an aerosol guard, comprised of a substantially aerosol-impervious material, interposed in the region between the upper surface of receiving plate and the lower surface of drip-director plate. While limiting the passage of aerosols and filtrate-associated residues, the cross-flow restrictor is adapted to permit a vacuum to be drawn therethrough.

With particular reference to the embodiment of FIGS. 2 and 3, a sheet-like cross-flow restrictor 30 is provided with an array of passages 32 complementary to the receiving well array and drip-director array that permit filtrate to pass from each microfiltration well 18 to a corresponding receiving well 26. Except for such passages, cross-flow restrictor 30 substantially fills the area between the confronting faces of the drip-director and receiving-well plates (14, 24). In this way, well-to-well movement of aerosols over the receiving plate 24 is substantially blocked. Consequently, the risk of cross-contamination presented by aerosol movement is substantially reduced. Additionally, aerosols formed at any one receiving well that inadvertently pass through the cross-flow restrictor (i.e., those that are not effectively blocked or trapped) will be pulled by the vacuum source through an adjacent aperture 28 down to the region below plate 24 without passing over the openings of neighboring receiving wells, as described more fully below.

Greater details about the cross-flow restrictor, methods of attaching the cross-flow restrictor, and materials useful for the restrictor, are described in U.S. Pat. No. 6,159,368, which is incorporated herein in its entirety by reference.

In another embodiment, the means for avoiding cross-contamination due to the well-to-well movement of aerosols includes vents or apertures 28 extending through the surface of receiving plate 24. In one preferred embodiment, at least one such aperture is disposed near each receiving well. It should be appreciated that a reduced pressure applied from below the plate will extend through the apertures to the microfiltration wells.

Greater details about the number of, positioning, and other characteristics about the aperatures can be found in U.S. Pat. No. 6,159,368, which is incorporated herein in its entirety by reference.

As previously noted, apertures 28 permit fluid communication between the regions above and below the receiving-well plate 24. Upon evacuating lower vacuum chamber 29, a vacuum will be established reaching from exit port 51 to the region between each microfiltration well and a corresponding receiving well. Particularly, the vacuum will pull along flow pathways extending from each microfiltration well 18 into the interface region between the confronting surfaces of drip-director plate 14 and receiving-well plate 24. The vacuum flow pathways then will cross downward through the surface 25 of the receiving plate, by way of respective vents 28, to the open reservoir of chamber 29. Here, the vacuum flow pathways will extend along the lower chamber until reaching exit port 51. Large, blackened arrows illustrate exemplary vacuum flow pathways in FIG. 3. Advantageously, aerosols and filtrate residues that become entrained in the vacuum flow are largely directed away from each receiving well area and out of the system without passing over neighboring receiving wells. Also, it should be appreciated that the vacuum pathways are directed in such a manner as to encourage a flow that is largely downward and laminar in nature. Cross-flow, and thus turbulence, is greatly minimized compared to most conventional arrangements.

The illustrated embodiments show a cross-flow restrictor 30 used in combination with a vented receiving-well plate 24, as just described. Notably, the cross-flow restrictor 30 covers the apertures 28, so that a vacuum pathway extending from the region between each microfiltration well 18 and corresponding receiving well 26 to the region below the receiving-well plate 24, via a nearby aperture 28, must pass through the cross-flow restrictor 30. Since the cross-flow restrictor 30 allows a vacuum to be drawn therethrough, but discourages the passage of aerosols, filtrate-associated aerosols are substantially separated (i.e., filtered out by the cross-flow restrictor) from the drawn vacuum and, thus, the potential for well-to-well movement of aerosols over the surface 25 of the receiving plate is even further reduced.

Greater details about using individual cross-flow constrictors can be found in U.S. Pat. No. 6,159,368, which is incorporated herein in its entirety by reference.

As previously mentioned, it is noteworthy that the vacuum flow pathways established between the regions above and below the receiving-well plate, in all of the embodiments described herein, are routed in a manner that encourages a largely laminar and downward flow (including any entrained gases and/or aerosols). Compared to most conventional arrangements, horizontal flow over the upper surface of the receiving-well plate is greatly minimized. Not only is this the case in the regions proximate the microfiltration and receiving wells, but it is also the case for the peripheral-edge regions of the plates. In this regard, and with particular reference to the embodiment of FIG. 3, the contact between the inwardly extending flap 44a of stepped gasket 44 and the top of ridge 48 of the receiving-well plate 24 is such that airflow therebetween is obstructed or baffled. Thus, upon evacuating the lower vacuum chamber 29, gases located above the stepped gasket 44, in the region denoted by arrow 46, will be drawn into the lower vacuum chamber via vent 28. Gases in the space under the lower surface of stepped gasket 44, denoted generally by the arrow 47, on the other hand, will be drawn into the lower vacuum chamber via a gap 49 provided between the receiving-well plate and the surface 50 about vacuum chamber 29. By limiting the extent of horizontal airflow across the receiving-well plate in this way, turbulence resulting from cross flow along the periphery of the arrangement is minimized.

An additional means for avoiding cross-contamination due to well-to-well movement of aerosols, as well as filtrate splattering, relates to the positioning of each drip director's lower opening relative to the upper rim, or lip, of a corresponding receiving well. According to this feature, the outlet port 16c of each drip director 16 extends downwardly from the drip-director plate 14 so as to enter into a corresponding receiving well 26. In this regard, the lower portion of each drip director 16 has a diameter that enables it to register with the open top of a corresponding receiving well 26 in the receiving plate 24. As shown in the embodiment of FIG. 3, the outlet port 16c of each drip director 16 is situated below the upper rim or lip of a corresponding receiving well 26. By placing the outlet port 16c at a region that is laterally surrounded by the inner sidewalls of the receiving well 26, much of the aerosol generated during filtration will impact upon the receiving-well walls, as opposed moving laterally over toward a neighboring receiving well. As an additional advantage, such placement of the drip-director outlets helps to reduce filtrate splattering.

According to various embodiments of the present invention, the present invention provides a method for avoiding cross-contamination due to well-to-well movement of aerosols in a multi-well microfiltration system. Greater details about such methods that draw a vacuum downward to avoid or minimize well-to-well movement are provided in U.S. Pat. No. 6,159,368, which is incorporated herein in its entirety by reference. It should be appreciated that the apparatus described above is particularly well suited for carrying out such methods. For example, a vacuum chamber, such as lower chamber 29 shown in FIG. 3, may be connected to a low pressure source, such as a vacuum pump (not shown), for establishing a pressure differential across filter elements 8a, 8b disposed in microfiltration wells 18. The reduced pressure, then, will cause filtrate to emanate from drip directors 16. Aerosol guard 30 provides a means to limit filtrate-associated aerosols formed from the filtrate at any one microfiltration well 18 from moving across the upper surface 25 of receiving-well plate 24 to a neighboring receiving well. Apertures 28, extending through the surface 25 of receiving-well plate 24, permit the vacuum to extend between each microfiltration well and the region below the receiving-well plate 24 without having to pass over the openings of neighboring receiving wells.

When evacuating the lower chamber, it is advantageous to slowly change (ramp) the pressure to a desired value, combined with the utilization of very low pressures (e.g., less than about 2 psi, and preferably less than about 1 psi), to further reduce the potential for cross-contamination, as by aerosols. For example, in going from ambient pressure to a value within the range of about 0.75 to about 2 psi, a ramp period of about 2–3 seconds is employed.

According to various embodiments of the present invention, a multi-well microfiltration arrangement is provided for enabling the flow of filtrate from each well, while avoiding cross-contamination due to pendent drops that may adhere to the drip directors of the various microfiltration wells. As previously mentioned, such pendent drops can fall into neighboring receiving wells when moving the discharge-conduit array or drip-director plate over the receiving array or receiving-well plate.

According to one embodiment, a microfiltration well is evacuated in the direction of its upper opening, thereby pulling any pendent drops of fluid hanging from its drip director back up into the well. To accomplish the evacuation, a pressure control source, e.g., a vacuum pump, in communication with an upper region of the mini-column is operable to evacuate the mini-column in the direction extending from the drip director to the upper opening.

According to various embodiments of the present invention, pendent drops hanging for the drip directors or discharge conduits are touched-off, whereby the pendent drops are moved to make contact with inner sidewalls of receiving wells or receiving holes of the receiving array. In this regard, the drip director outlets of all the microfiltration wells are simultaneously brought into contact with the inner sidewalls of corresponding receiving wells.

Means are provided for effecting relative movement between the discharge-conduit array or drip-director plate, and the receiving array or receiving-well plate, for simultaneously moving the discharge conduits proximal to, or into contact with, and distal from or out of contact with, the inner walls of the respective receiving wells or receiving holes.

According to various embodiments of the present invention, a device is provided for shifting the receiving array along a plane substantially orthogonal to the longitudinal axes of the receiving wells or receiving holes of the receiving array, while the discharge conduits are maintained in a substantially fixed position. In other various embodiments, the device for effecting relative movement is operable to shift the discharge-conduit array along a plane substantially orthogonal to the longitudinal axes of the receiving wells or receiving holes of the receiving array, while the receiving wells are maintained in a substantially fixed position.

An exemplary arrangement for effecting relative movement is depicted in FIGS. 7 through 10. With initial reference to FIGS. 7 and 8, an L-shaped carriage, as denoted by the reference numeral 60, is provided with a central opening 62 configured to receive and support a multi-well microfiltration assembly, indicated generally as 6, from above. Below carriage 60, a receiving-well plate 24 having an array of receiving wells 26 is supported in a lower vacuum chamber (not shown).

Carriage 60 is mounted on a pair of parallel longitudinal carrier rails for reciprocal linear movement along a first, substantially horizontal, axis. In the illustrated embodiment, one of the carrier rails is a linear bearing rail, denoted as 64, which supports the carriage 60 via an interposed linear bearing member 65 attached to the lower surface of the carriage 60 toward one lateral edge. The other carrier rail is a U-shaped bearing guide, denoted as 66, that receives a bearing wheel 68, extending laterally outward from the other edge of the carriage 60, in an elongated track or slot 66a.

Carriage 60 is moved along the rails 64, 66 by a belt assembly comprised of a flexible belt 70 having its ends attached at each longitudinal end of a U-shaped bracket 74 forming a part of a spring-loaded movement-control mechanism 72, described more fully below. Belt 70 is passed around a driven roller 76 and an idler roller 78, disposed proximate longitudinally opposing ends of the carrier rail arrangement. To prevent against slippage, the belt may be provided with teeth 70a adapted for mating engagement with complementary sets of teeth 76a, 78a on the rollers.

Driven roller 76 is in mechanical communication with a motor, such as 82, through a power train assembly, as indicated generally by the reference numeral 84. When motor 82 is energized, belt 70 will move, causing carriage 60 to slide along the carrier rails 64, 66, with the direction of movement depending on the rotation of the drive shaft 86 extending from motor 82. Motor 82 may be of any suitable, known type, e.g., a stepper motor, servo motor, or similar device. In place of the motor, a manually operable drive system can be used for providing movement of the various components along respective paths to accomplish touch-off and transfer operations. In various manually-operable embodiments of the present invention, the motor is replaced with a manually-operable handle that actuates the roller, for example, through a transmission system, wherein the handle can be a lever, two or more levers, a bar, a knob, or any other suitable manually-operable actuator.

Stepping the motor 82 causes belt 70 to move around rollers 76, 78, with the direction of movement dependent upon the direction of rotation of the motor's shaft 86. Movement of belt 70, in turn, causes carriage 60 to slide along guide rails 64, 66, thereby shifting the drip director array 16 laterally with the respect to the receiving well array 26. If the drip directors 16 are positioned so that they extend into respective receiving wells 26, sufficient stepping in a given direction will cause the drip directors 16 to engage the upper, inner surfaces of the receiving wells 26, as shown in the sectional views of FIGS. 9(A)–9(C). In this way, pendent drops of filtrate hanging from the drip directors 16 are "touched off" to the inner surfaces of respective receiving wells 26. Similarly, upon reversing the stepping direction, the drip directors 16 can be moved to engage the upper, inner surfaces on the opposing side of the receiving wells 26 to further ensure effective touching-off of pendent drops. Greater details about motorized operation of the touch-off devices according to various embodiments of the present invention can be found in U.S. Pat. No. 6,159,368, which is incorporated herein in its entirety by reference.

Carriage additionally supports means for moving and positioning the microfiltration arrangement 6 along a second, generally vertical, axis. With particular reference to the embodiment of FIG. 7, a vertical-positioning mechanism is disposed on the upper surface of carriage along each lateral side of the microfiltration arrangment. Each vertical-positioning mechanism includes (i) lift springs, such as 92, that provide a continuous, upwardly-directed force tending to raise the microfiltration arrangement 6 to an elevated position whereat the drip directors 16 fully clear the upper lips of the receiving wells 26, and (ii) fluid cylinders, such as 94, that are operable to lower the microfiltration arrangement 6, against the force of the lift springs 92, to a seated position whereat each drip director 16 extends into the upper region of a respective receiving well 26. At its fully seated (lowered) position, the microfiltration arrangement 6 forms a seal with the lower vacuum chamber (not shown).

Both the springs 92 and the fluid cylinders 94 engage, at their upper ends, handles, denoted as 96, that extend upwardly and outwardly from each lateral side of the microfiltration arrangement's supporting frame 38. In one embodiment, the spring/cylinder arrangements are operable to hold the microfiltration arrangement at any one of three positions: (i) an open, upper, or travel position, (ii) an intermediate touch-off position, and (iii) a sealed or lower position. Manually-operable vertical positioning systems can be used and are described in more detail below.

Another exemplary arrangement for effecting relative movement of the discharge conduits and the receiving wells or receiving holes is depicted in FIGS. 11–17. According to various embodiments of a device according to the present invention, a means or device for effecting the relative movement is provided. The device includes a manually-operable mechanism, referred to herein as a handle, to shift the discharge-conduit array, or alternatively, the receiving array, relative to the other along a plane substantially orthogonal to the longitudinal axes of the discharge conduits. The handle can be a locking two-lever handle, for example. In such an embodiment, an operator places the discharge-conduit array or purification tray into the microfiltration apparatus while the apparatus is in the open position shown in FIG. 11. The operator then depresses the handle to thereby bring the discharge or distal ends of the discharge conduits to a point below the plane of the upper opening of the respective receiving wells. In this position, the distal ends of the discharge conduits, or the purification tray of which they are a part, can be manually shifted as described herein by application of a manual force to a handle connected to the discharge-conduit array. The movement of the handle can effect a touching-off operation, a vacuum sealing operation, a release operation, a station shift operation, or the like. The touch-off is accomplished, for example, by causing pendent drops of fluid hanging from the distal ends of the discharge conduits to contact the inner sidewalls of the receiving wells. The shifting can be done in a single movement, a double movement, or multiple movements, depending on the choice of the operator and the particular properties of the filtrate, such as viscosity, or the amount of precipitate present.

According to various embodiments of the present invention, it is not necessary for the distal ends of the discharge conduits to physically touch the sidewalls of the receiving wells, if the pendent drops contact the inner sidewalls of the receiving wells. The important aspect of these embodiments of the present invention is to achieve the complete transfer of each drop into the correct receiving well, and breaking the surface tension of the drop may be sufficient to achieve a gentle transfer without requiring the drip director or discharge conduit itself to touch the inner sidewall of the respective receiving well. According to various embodiments of the present invention, "touching-off" refers to contacting of the pendent drops alone to the sidewalls of the receiving wells. According to various embodiments of the present invention, touching-off refers to contacting the distal tips of the discharge conduits and touching the pendent drops to the corresponding inner sidewalls.

Figure 9A:
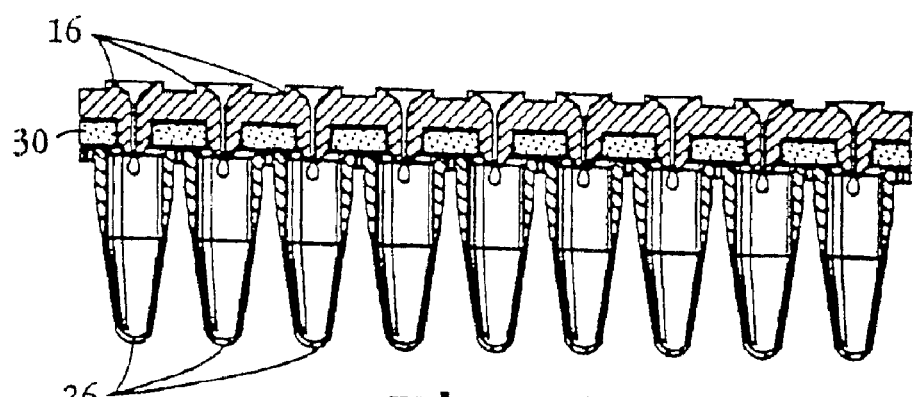
FIGS. 9(A)–9(C) are cross-sectional side views showing a touch-off operation according to an embodiment of the present invention whereby a plurality of discharge conduits from a discharge-conduit array is laterally shifted to the right and to the left to cause contact between pendent drops hanging from the discharge conduits and inner sidewalls of the respective receiving wells.
Figure 9B:
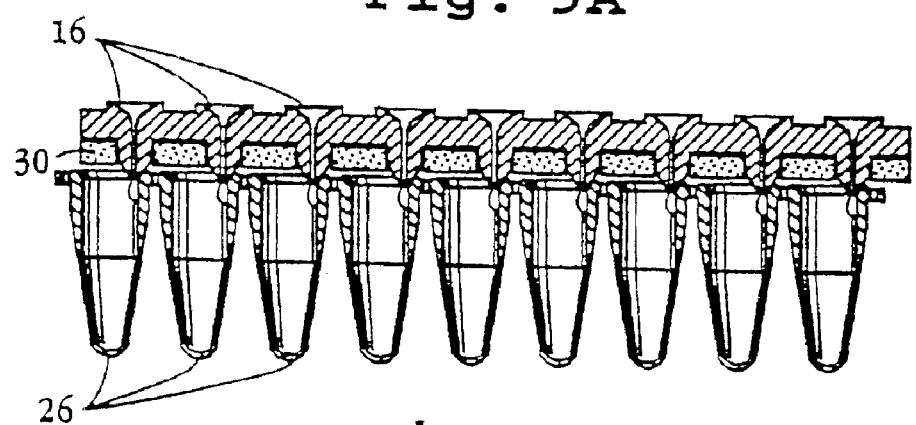
Figure 9C:
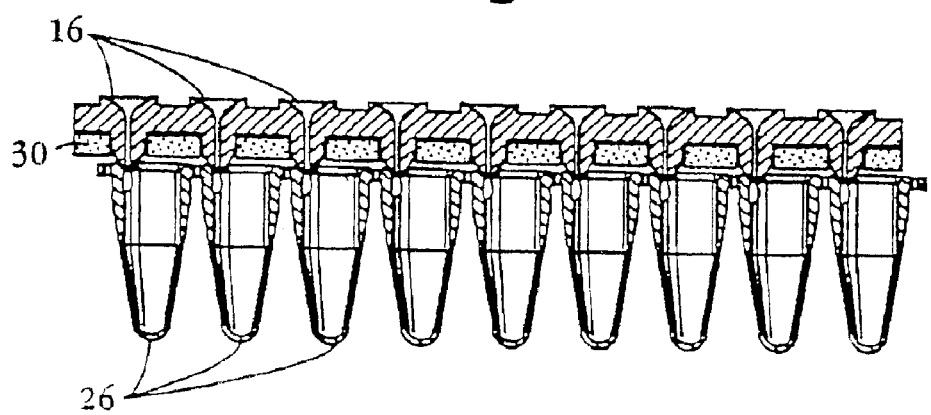

The touching-off (also referred to herein as the "touch-off operation") is illustrated in FIGS. 9A, 9B, and 9C. In FIG. 9A, the distal ends of the discharge conduits (also referred to herein as the drip directors) are shown positioned in the center of and above the corresponding receiving wells. In FIG. 9B, the distal ends of the discharge conduits are shown in contact with the right side of the corresponding receiving wells. In FIG. 9C, the distal ends of the discharge conduits are shown in contact with the left side of the corresponding receiving wells. Thus, according to an embodiment of the present invention, the purification tray or array of discharge conduits can be manually translocated from the position illustrated in FIG. 9A to the position illustrated in FIG. 9B to initiate the touching-off operation. The array of discharge conduits can then be manually translocated from the position illustrated in FIG. 9B to the position illustrated in FIG. 9C to continue and eventually complete the manual touching-off operation.

The touch-off operation may be carried out with the microfiltration arrangement 6 disposed at any position along the second (vertical) axis, provided only that the drip directors 16 extend at least partially down into the receiving wells 26. In one embodiment, touching-off of the drip directors 16 to the inner sidewalls of the receiving wells 26 is effected with the microfiltration arrangement 6 slightly raised above its fully seated position so that the lowermost regions of the drip directors 16, proximate their outlets 16c, will abut the inner surfaces of the receiving wells 26.

Thus, in an embodiment of the present invention is presented a discharge-conduit array including an array having a first plate having a plurality of columns, each column having a filter medium and being positioned over a second plate having a plurality of discharge conduits, whereby the discharge-conduit array is placed in a microfiltration apparatus of the present invention including a plurality of receiving wells, each receiving well positioned to receive filtrate from a corresponding distal ends of the discharge conduits, and whereby the discharge-conduit array is manually translocated in a generally horizontal manner in either of two directions from a reference "home" position along a generally horizontally extending axis, and then the discharge-conduit array is returned back to the reference "home" position, such that manual touching-off is achieved.

The region of each drip director 16 proximate its outlet may be shaped, e.g., angled or chamfered about its lower circumference, to promote the localization of any pendent drops of filtrate to certain regions of the drip director 16 and to optimize contact between such regions with the inner sidewall of a corresponding receiving well 26 during touch off. Similarly, the upper region of each receiving well 26 may also be shaped, e.g., in a manner complementary to (i.e., matching) a shaped drip director 16, so that adequate contact is made between these elements during touch off for substantially ridding the drip director 16 of any pendent drops of filtrate. In one preferred embodiment, as can be seen in FIGS. 9A–C, the upper, region of each receiving well is formed with an outwardly angled inner sidewall that matches an inwardly angled outer surface along the lower region of a corresponding drip director, thereby providing a substantial abutting surface between these elements during a touch-off necessary. That is, the drip directors 16 might be moved into engagement with the inner walls of the receiving wells 26, with continued pressure to move beyond the inner walls. Greater details about motorized control of the touch-off procedure and overshoot considerations are described in U.S. Pat. No. 6,159,368, which is incorporated herein in its entirety by reference.

In one embodiment, the movement-control mechanism includes a spring disposed such that movement of the carriage in either direction along the first axis will put the spring under compression. With particular reference to the partially schematic top plan views of FIGS. 10(A)–(C), the U-shaped bracket 74 that forms a part of the belt assembly is rigidly connected to a housing 101 containing large and small bores, respectively indicated generally as 102 and 108. Bore 102 has a large-diameter portion 102a and a small-diameter portion 102b, separated by a radial step 102c. A stepped-diameter shaft, indicated generally as 104, having a large-diameter portion 104a and a small-diameter portion 104b, separated by a radial step 104c, passes through bore 102 and rigidly attaches, at its large-diameter end, to an extended-arm portion 60a of the L-shaped carriage 60. A guide pin 106, which assists in maintaining the substantially horizontal orientation of carriage 60, rigidly attaches to the extended arm portion 60a of carriage 60 at one end and is received in small bore 108 at its other end. Inside the large-diameter portion 102a of bore 102, a spring 110 concentrically mounts the small-diameter portion 104b of shaft 104 between a pair of spaced washers, denoted as 112 and 116. The two washers 112, 116 are concentrically mounted for sliding movement along the small-diameter portion 104b of stepped shaft 104. Spring 110 urges the two washers 112, 116 toward opposite, extreme ends of the small-diameter portion 104b of shaft 104. A fixed-position washer 114 is seated within a circumferential groove (not shown) formed in the small-diameter portion 104b of shaft 104 near its free end.

Figure 10A:
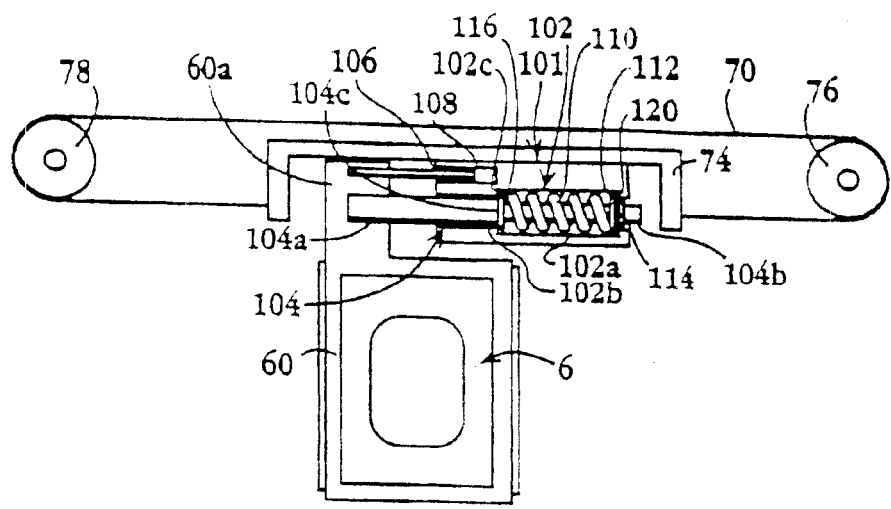
FIG. 10(A) is a partially schematic top plan view showing a spring-loaded touch-off mechanism in its normal, or neutral, position.
Figure 10B:
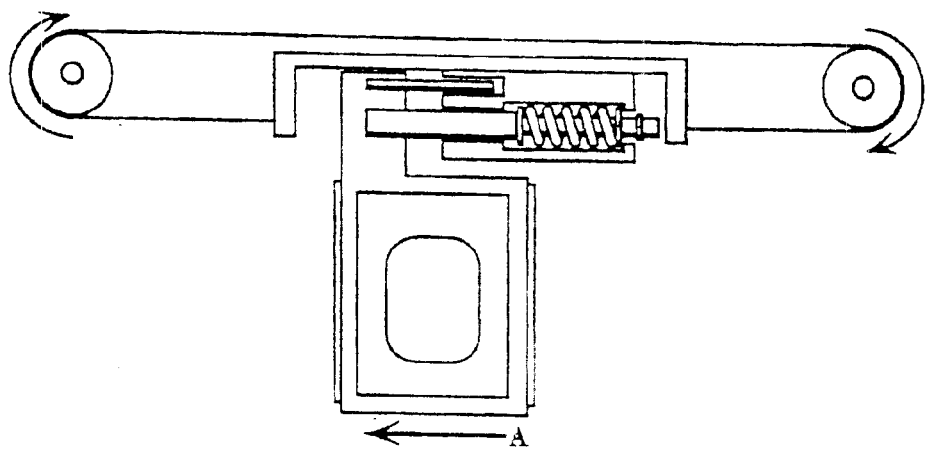
FIG. 10(B) is a partially schematic top plan view showing the spring-loaded touch-off mechanism of FIG. 10(A) in a first, shifted position.

When belt 70 moves U-shaped bracket 74 in the direction indicated by the arrow "A," in FIG. 10B, bore 102 slides along shaft 104 in a direction toward the extended arm 60a of carriage 60. As a result, an annular lip 120 that extends radially inward at the end of bore 102 acts against an annular, peripheral region of washer 112, causing the washer 112 to slide along the small-diameter portion 104b of stepped shaft 104, thereby compressing spring 110. When the compression force overcomes the pre-loaded retaining force, carriage 60 will then shift in the same direction (direction "A").

Figure 10C:
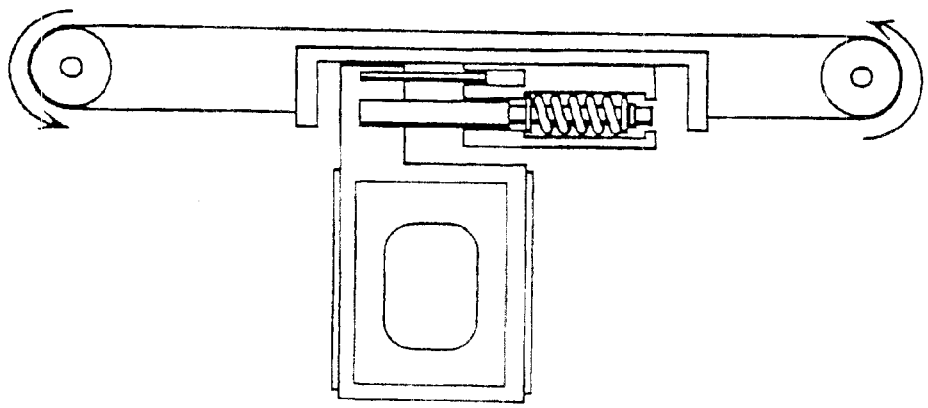
FIG. 10(C) is a partially schematic top plan view showing the spring-loaded touch-off mechanism of FIGS. 10(A) and 10(B) in a second, shifted position.

When belt 70 moves U-shaped bracket 74 in the direction indicated by the arrow "B," in FIG. 10C, bore 102 slides along shaft 104 in a direction away from the extended arm 60a of carriage 60. As a result, the radial step 102c of bore 102 acts against an annular, peripheral region of washer 116, causing the washer 116 to slide along the small-diameter portion 104b of stepped shaft 104, thereby compressing spring 110. When the compression force overcomes the pre-loaded retaining force, carriage 60 will then shift in the same direction (i.e., direction "B").

In an embodiment, spring 110 provides a pre-load force of about 1 pound. Thus, the force provided by the stepper motor 82 will not be effective to move the carriage 60 until the threshold of about 1 pound is overcome. Advantageously, the arrangement provides (i) a constant-hold mode at the center, or neutral, position, and (ii) a constant-force mode for effecting touch off. The spring 110 provides compliance in the system, e.g., allowing touch-off to start at 1 pound and end at 1.2 pounds.

With reference to the apparatus as described above, one preferred embodiment of the present invention contemplates the following steps:

(i) microfiltration arrangement 6 is loaded onto carriage 60 and clamped in place;

(ii) carriage 60 is centered over a lower vacuum chamber 29;

(iii) microfiltration arrangement 6 is lowered to its seated position (e.g., by retracting fluid cylinders 94) and sealed over the lower vacuum chamber 29;

(iv) a vertical positioning apparatus or system (not shown) lowers upper vacuum chamber 20 against the top of microfiltration arrangement 6 and, optionally, applies a downward force, e.g., about 5 pounds, to the stacked arrangement;

(v) lower vacuum chamber 29 is evacuated (e.g., at about 0.5–3 psi) to effect elution/purification;

(vi) carriage 60 is raised slightly from its fully seated position to a touch-off height whereat only the lowermost regions of the drip directors 16 extend below the upper lips of the receiving wells 26;

(vii) a manually-operated drive device is used to move the drip directors in a forward direction to touch off the drip directors 16 to a sidewall of the receiving wells 26;

(viii) the manually-operated drive device is used to move the drip directors in a reverse direction to touch off the drip directors 16 to the opposing inner sidewalls of the receiving wells 26;

(ix) forward and reverse movements are repeated to perform each of the touch-off steps once more;

(x) carriage 60 is re-centered over lower vacuum chamber 29;

(xi) microfiltration arrangement 6 is lowered to its seated position and sealed over lower vacuum chamber 29;

(xii) optionally, a downward force of, for example, about 5 pounds, can be applied to the stacked arrangement;

(xiii) upper vacuum chamber 20 is evacuated to effect a pull-back of pendent drops (e.g., at about 0.1–0.3 psi);

(xiv) microfiltration arrangement 6 is raised to its fully elevated position so that the drip directors 16 fully clear the receiving wells 26; then (xv) carriage 60 is moved to next station.

Figure 16:
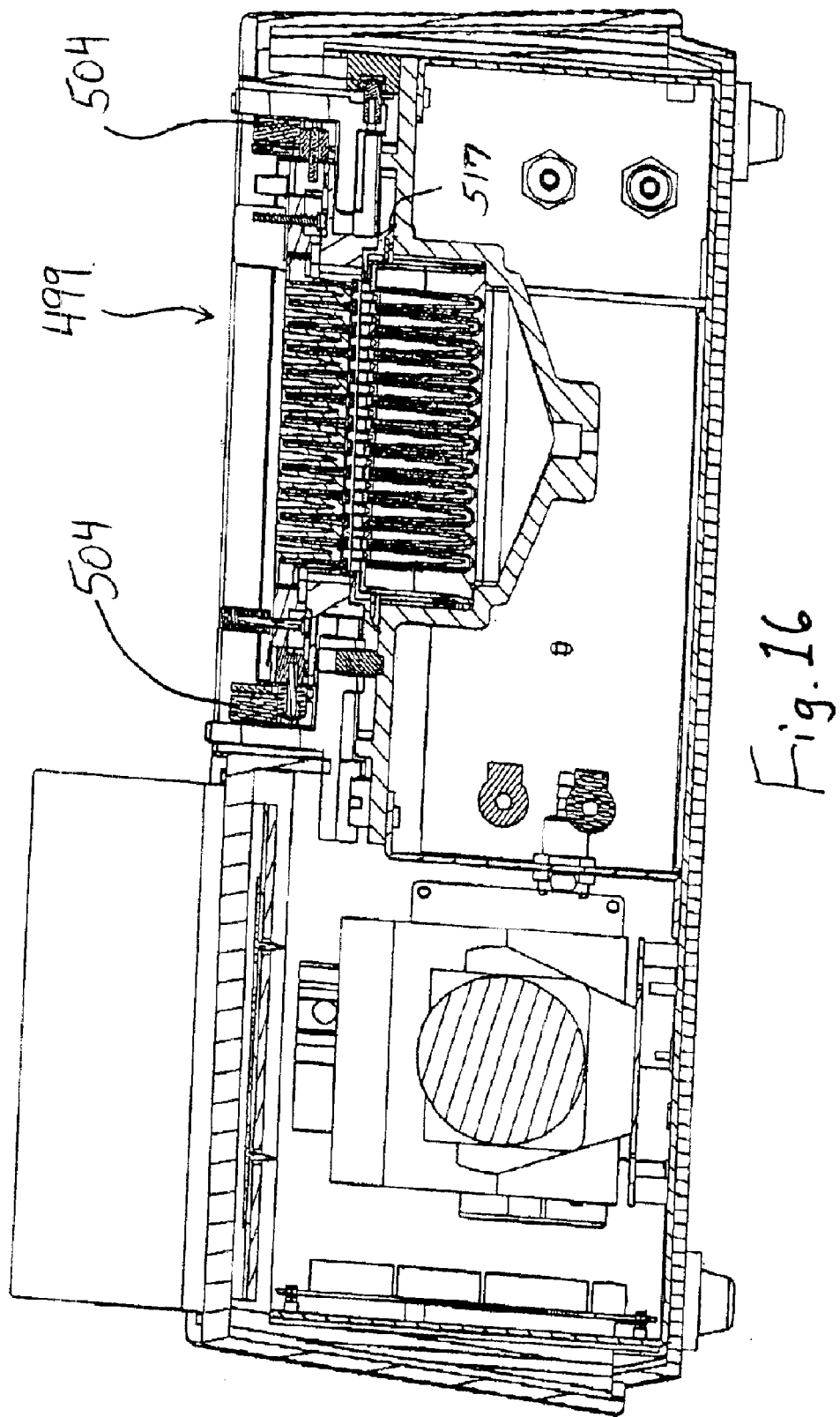
FIG. 16 is a cross-sectional front view of a device according to an embodiment of the present invention with the carriage and a deep-well discharge-conduit array in the lowered position and the handle in the set position.

FIG. 16 of U.S. Pat. No. 6,159,368 shows an automated work station to carry out these steps in an automated fashion.

Also useful as part of the microfiltration apparatus of the present invention is software containing a software program, and a software-reading device or software-implementing means, within or externally connected to the microfiltration apparatus, wherein the software contains at least one algorithm which can control through the software-reading device or software-implementing means the pressure differential operations of the apparatus. In an embodiment of the present invention, embedded software controls all differential pressure operations, such as vacuum and positive pressure operations, to thereby precisely set at least a pressure differential or partial vacuum above or below the distal ends of the discharge conduits, the duration of the partial vacuum, and pressure levels, control start and stop actions, allow the operator to create individualized methods, specify users, display run logs on a digital or visual display, and diagnose the system. The software can be programmed to allow the operator of the microfiltration apparatus to store in the memory of the software-reading device methods and conditions for future reference, repetition, and/or modification.

With regard to spatial orientation, it should be noted at this point that the various components (e.g., upper chamber, mini-column plate, filter element, drip-director plate, frame, cross-flow restrictor, receiving-well plate, and lower chamber) are illustrated and described herein as being stacked in vertical relationship, with the upper vacuum chamber being the topmost component. Further, each microfiltration well is described as having a central axis disposed in a substantially vertical fashion, with a flow pathway extending downwardly through the well. It should be noted, however, that these orientations have been adopted merely for convenience in setting forth the detailed description, and to facilitate an understanding of the invention. In practice, the invention contemplates that the components and wells may be disposed in any orientation.

Methods of covering and sealing receiving arrays, for example, can be found in U.S. Pat. No. 6,159,368, which is incorporated herein in its entirety by reference, particularly in FIGS. 11–14 of the Patent. Automated handling and work stations to carry out many of the aforementioned and/or additional methods are described in greater detail in U.S. Pat. No. 6,159,368, particularly with respect to FIGS. 16–24 of the Patent.

According to various embodiments of the present invention, the features, relationships of arrays, and touch-off methods described herein, particularly above, are used in a manually-operated workstation, in particular, to provide a manually-operable multi-well microfiltration apparatus and method. Exemplary manually-operable apparatus according to various embodiments of the present invention are shown in FIGS. 11–27.

According to various embodiments of the present invention, the discharge-conduit array and the corresponding carriage of the device can occupy at least three vertical positions, for example, an open position, a sealed position, and a touch-off position. The open position is shown, for example, in FIGS. 11, 19, 22, and 25, which depict a multi-well microfiltration apparatus according to various embodiments of the present invention. In the open position, a discharge-conduit array with samples can be loaded into or removed from the apparatus. As can be seen, the distal tips 570 of the discharge conduits 510 of the discharge-conduit array 500 horizontally clear the receiving wells 502 of a receiving well array 590. FIG. 11 is a partial side cross-sectional view in partial breakaway of a device 499 according to an embodiment of the present invention with a discharge-conduit array 500 in a beginning or open position. The relationship between the discharge-conduit array and the receiving array can be seen, for example, in greater detail with reference to FIGS. 24–26, particularly in FIG. 25 which depicts the open position. In the open position, shown enlarged in FIG. 25, a gap 551 exists between the bottom 562 of a deformable apron 517 on the discharge-conduit array carriage 500, and the top surface 564 of a receiving array platform 566. The distance between the discharge conduit array 500 and the receiving array 590 enables the discharge-conduit array 500 to move horizontally and clear the receiving array 590. This distance is eliminated when the apparatus is in the sealed position, as shown, for example, in FIGS. 13, 16, 20, 23, and 26. The touch-off position is exemplified in FIGS. 12, 14, 15, 17, 18, 21, 24a, 24b, and 27.

Many of FIGS. 11–27 depict apparatus including two or more treatment stations. FIG. 11, for example, shows a discharge-conduit array carriage assembly 600 positioned to axially align the discharge conduits 510 of the discharge-conduit array 500 with corresponding receiving wells 502 of a receiving well array 590, at a first treatment station 610. According to various embodiments of the present invention, the discharge conduit array can be shifted while in the open position, with the carriage assembly 600, to align the discharge-conduit array with a second receiving array 592 of receiving wells 508 at a second treatment station 612. The carriage assembly 600 can be moved from the first treatment station 610 to the second treatment station 612, and back to station 610, as for example, by a sliding engagement with a rail or track 506 from station 610 to station 612.

Station 610 can be useful, for example, for archiving, collecting, or filtering samples. Station 612 can be useful, for example, for washing material from a sample, disposing of undesirable material, and/or collecting waste from a sample or samples. As such, station 612 can be connected to a waste receptacle able to receive waste that is expelled from the distal ends 570 of the discharge conduits 510 and into the waste receiving wells 508.

FIG. 11 depicts an open position of the device with the distal ends 570 of the discharge conduits 510 of the discharge-conduit array 500 positioned above and outside the upper opening of the respective receiving wells 502. In this open position, of the device according to an embodiment of the present invention, the discharge-conduit array 500 can be manually moved along track 506 to the station 612 and aligned over the receiving wells 508.

The handle 504 shown in the drawings is provided with a releasable mechanism to lock the handle in the open or sealed positions. The Figs. also show a secondary clamp 512 for locking the carriage in the intermediate position.

Figure 21:
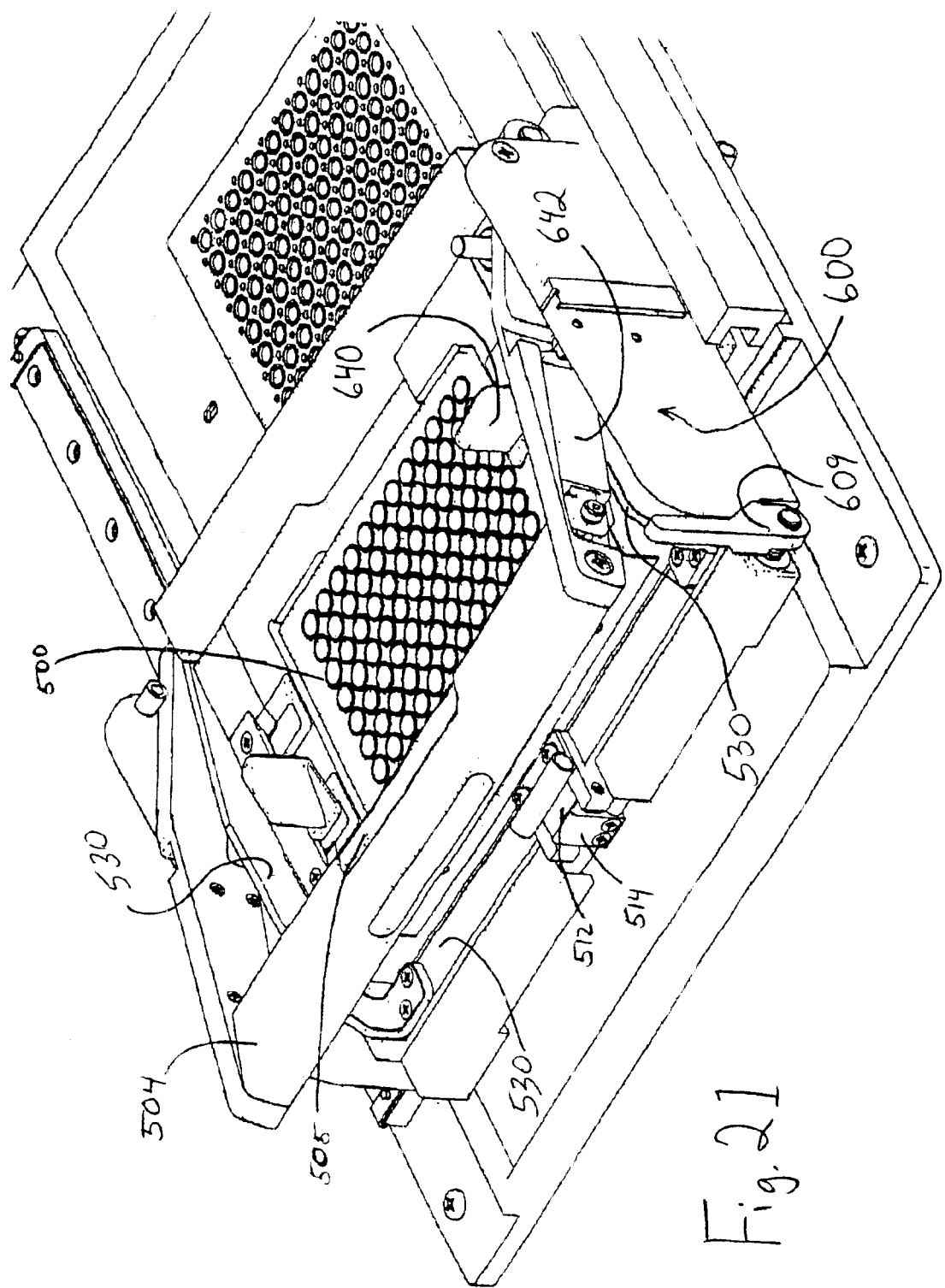
FIG. 21 is a perspective view of a device according to an embodiment of the present invention showing the carriage and discharge-conduit array at a first treatment station in the touch-off position.
Figure 22:
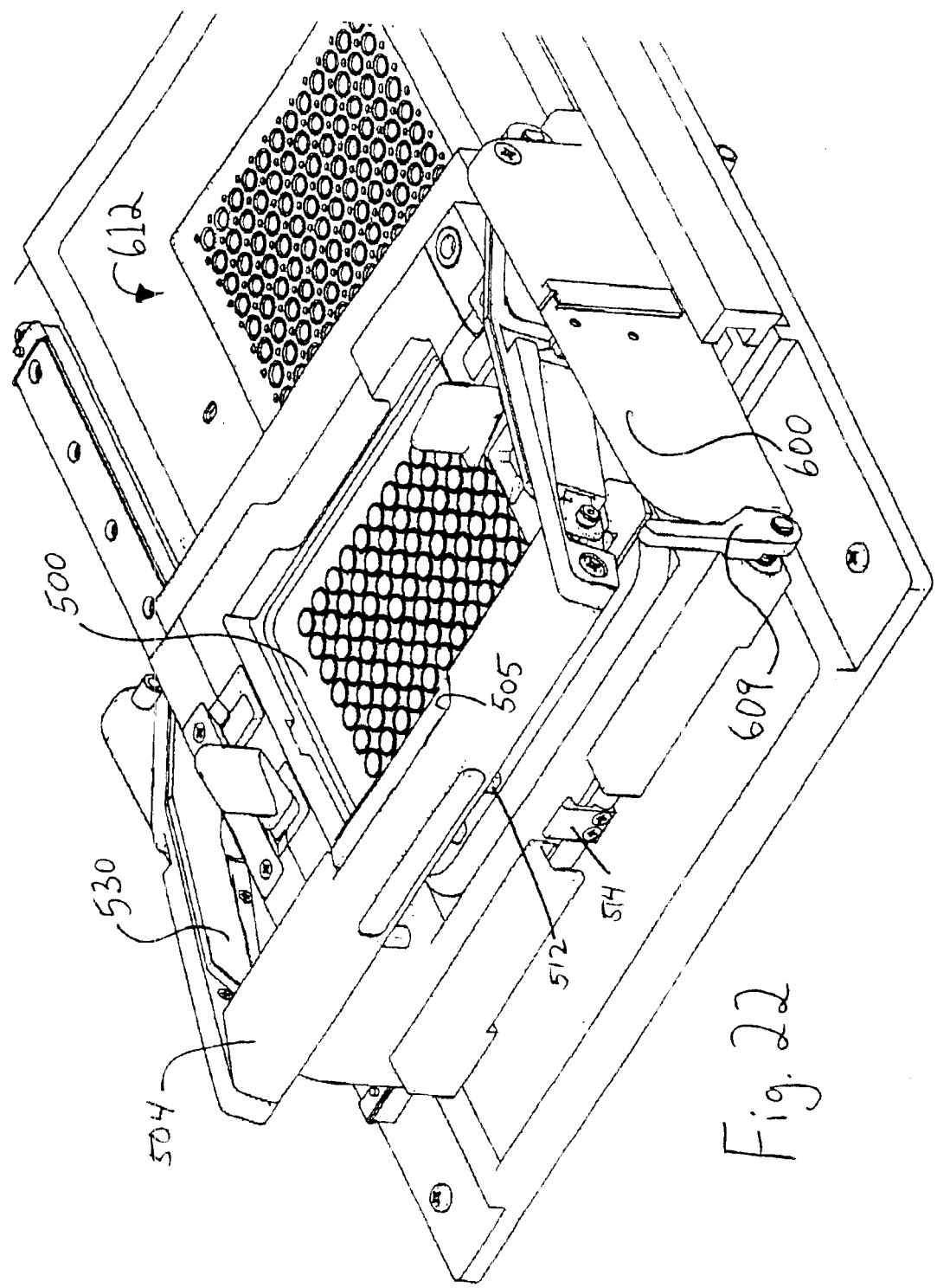
FIG. 22 is a perspective view of a device according to an embodiment of the present invention showing the carriage and discharge-conduit array in the elevated or open position and the handle in the beginning or release position.
Figure 23:
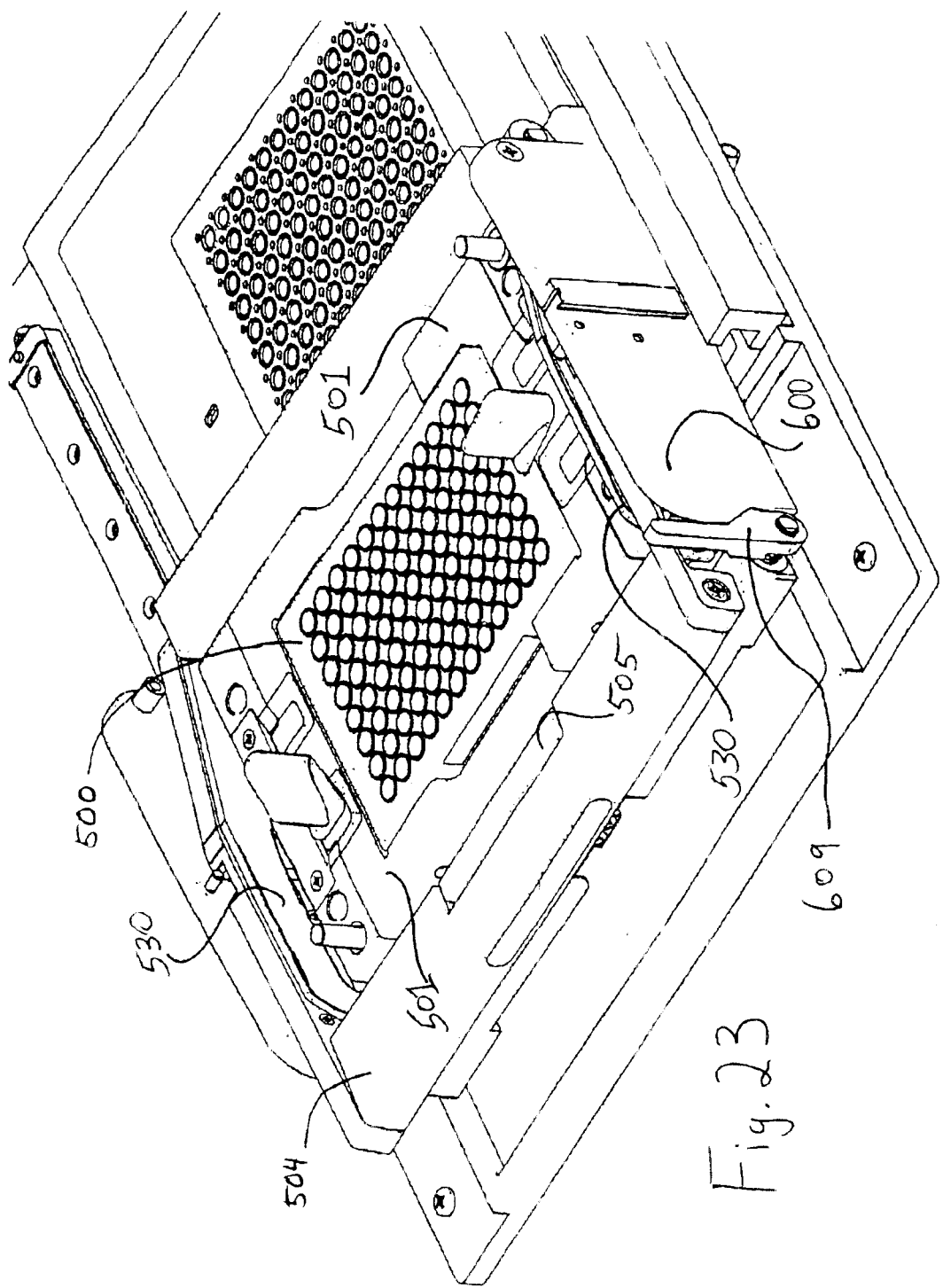
FIG. 23 is a perspective view of a device according to an embodiment of the present invention showing the carriage and discharge-conduit array in the lowered or sealed position and the handle in the set position.

The Figures, including FIGS. 21–23, illustrate the operation of the two-levered, manually-operable handle and its relationship to the vertical positioning assembly 501. In the open position shown in FIGS. 22 and 25, the two-levered handle is up and secondary clamp 512 is released from latch 514. When both the handle 504 and connecting arm 530 of secondary clamp 512 are depressed sufficiently, a locking mechanism in conjunction with catch arm 642 latches the vertical positioning assembly in a fully depressed position for vacuum discharge. Squeezing release mechanism 505 toward handle 504 releases the locking mechanism in conjunction with catch arm 642 and allows the handle 504 to be lifted to an elevated position. When the handle 504 is in the elevated position and vertical positioning assembly 501 is in the touch-off position, the secondary clamp 512 is not released from latch 514 such that the vertical positioning assembly 501 and the discharge-conduit array 500 are positioned with the discharge conduit nozzle tips at or just inside the open upper ends of the respective receiving wells, and slightly elevated with respect to their positions in the closed or sealed position. Activation of latch 609 releases latch 514 from secondary clamp 512 and enables the vertical positioning assembly 501 and the discharge conduit array to be lifted to an even further elevated open or station transfer position. In operation, handle 504 pivots about pivot point 520, whereby handle 504 can be raised to set the discharge-conduit array 500 in position for manual touching-off. No touching-off can occur in the open position depicted in FIG. 11 because the distal ends 570 (drip directors) of the discharge conduits 510 are not positioned within or near the openings of the receiving wells 502.

A biasing device 507, such as a torsion spring or compression spring, in mechanical communication with a release mechanism 505 within the handle 504, biases the handle 504 into a locked position whereby the discharge-conduit array 500 cannot be shifted. In response to a compressive manual force applied by an operator to the release mechanism 505 and against the bias of the biasing means 507, the locked position of the handle 504 is disengaged. The release mechanism 505 works to transmit a force through an arm 642 as shown, for example, in FIGS. 21 and 27 to a vertical positioning assembly lock release position. Activating the release mechanism 505 allows the handle 504 to be elevated to an elevated position, whereby the carriage can be moved into an intermediate touch-off position. Once in the elevated position, the handle 504 can then be manually pushed and pulled for touch-off. From the touch-off elevated handle position, the release mechanism 609 can be activated to release a second lock or a second release mechanism, to unlock or release the carriage, resulting in a freedom of the carriage to move into an elevated, beginning, open, release position, for example, against a biasing mechanism. Handle 504 pivots about pivot point 520 allowing handle 504 to be raised and lowered.

In operation, handle 504 is manually gripped by an operator of the microfiltration apparatus. The manually-applied horizontal force can be used to horizontally shift the discharge-conduit array 500, for example, for a touch-off operation. Additionally, or in the alternative, the discharge-conduit array 500 can be released to permit manual moving by an operator from the first station 610 to the second station 612.

Figure 12:
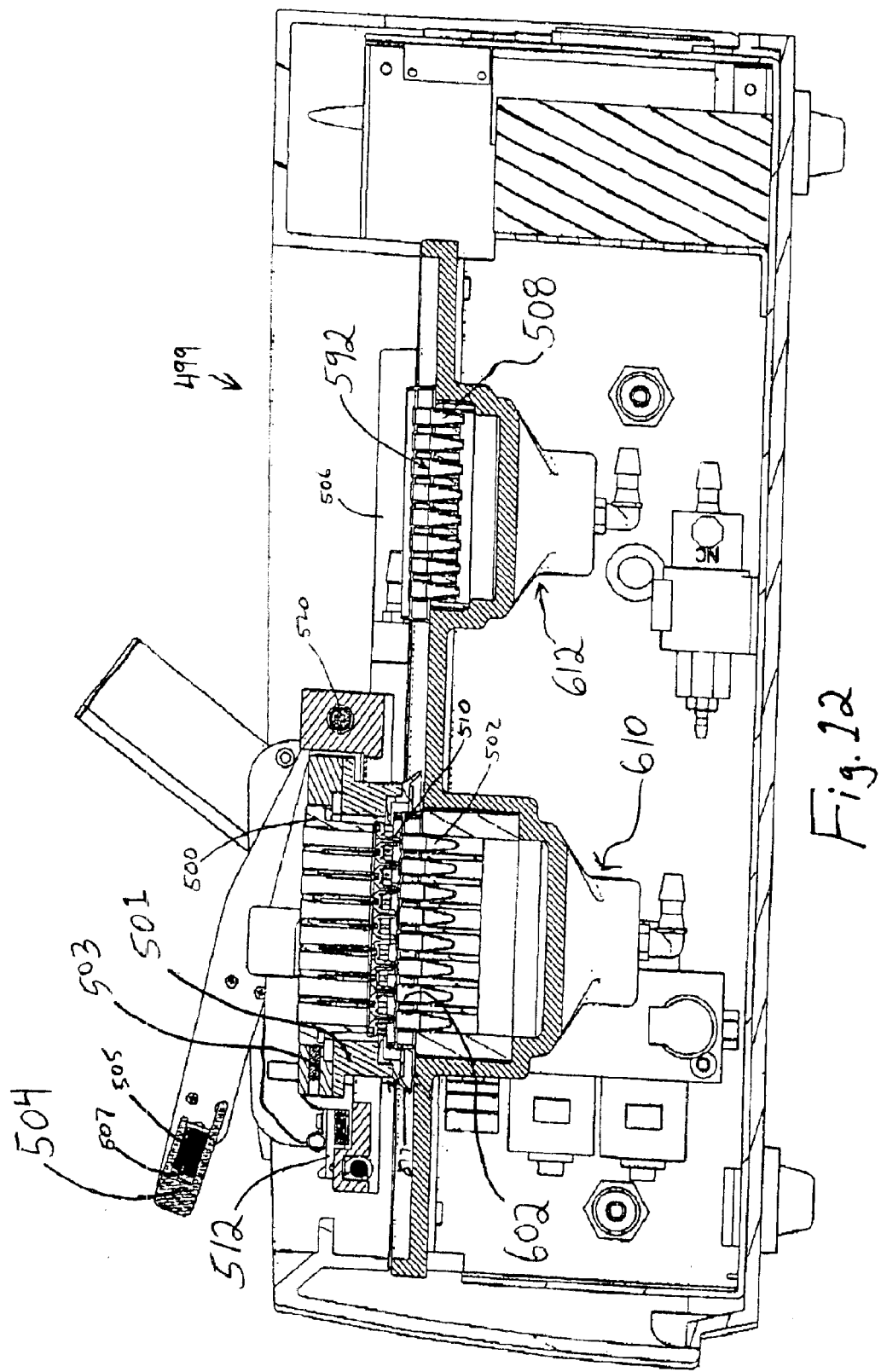
FIG. 12 is a cross-sectional side view in partial breakaway of a device according to an embodiment of the present invention with the carriage and discharge-conduit array in the touch-off position.

FIG. 12 is a partial side cross-sectional view in partial breakaway of a device 499 according to an embodiment of the present invention having the discharge-conduit array 500 in the touch-off position. In FIG. 12, the discharge-conduit array 500 is located at station 610 above the receiving wells 502. Touching-off can also be performed when the discharge-conduit array 500 of FIG. 12, is located at station 612. In FIG. 12, the handle 504 is in the raised position and the secondary clamp 512 is in the lowered and secured position. The distal ends of the discharge conduits 510 of the discharge-conduit array 500 are positioned directly above the receiving wells 502 and extending below the upper plane defining the upper openings of the respective receiving wells 502.

In any suitable position the discharge-conduit array 500 can receive reactants, such as DNA materials, reagents, lysing agents, and the like. After a pressure differential, if any, is applied, the discharge-conduit array 500 can be manually advanced slightly by sliding the discharge-conduit array 500 in a direction toward the right in FIG. 12, then manually retracted by pulling the handle 504 connected to the discharge-conduit array 500 backward to the left in FIG. 12. The extent of the movement or translocation of the discharge-conduit array 500, the distance is limited by the contacting of, or a provision not to contact, the distal ends 570 of the discharge conduits 510 with the inner sidewalls 602 of the receiving wells 502, 508 or 524. Gap 550 is much smaller in the touch-off position of FIG. 12 than the gap 551 shown in the open position of FIG. 11. Gap 550 in the touch-off position of FIG. 14, can be, for example, from about 0.01 inch to about 0.1 inch, for example, about 0.07 inch.

Figure 13:
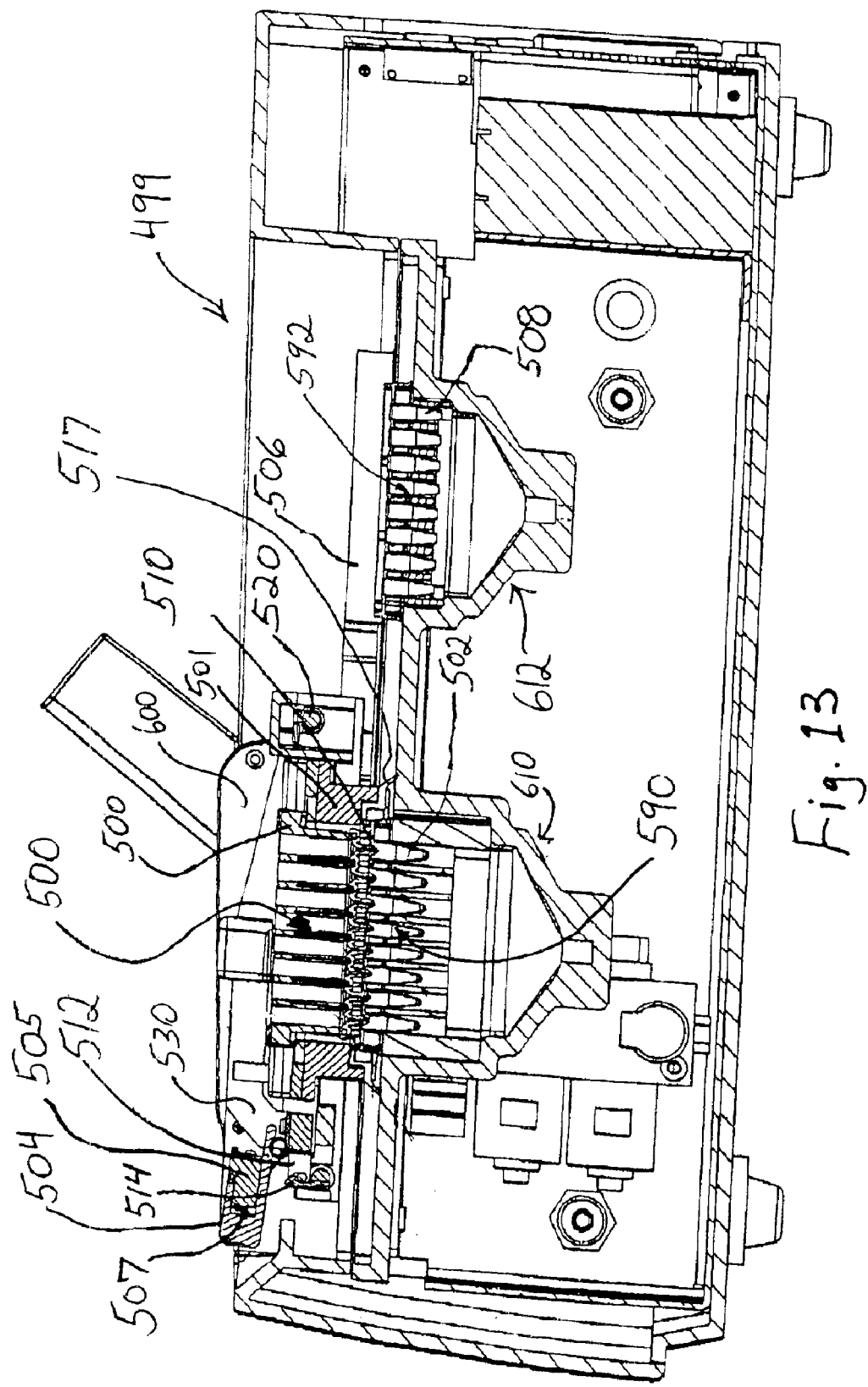
FIG. 13 is a cross-sectional side view in partial breakaway of a device according to an embodiment of the present invention with the carriage and discharge-conduit array in the lowered position and the handle in the set position.

FIG. 13 is a partial side cross-sectional view in partial breakaway of a device 499 of an embodiment of the present invention with the discharge-conduit array 500 in the sealed position. In this position, the secondary clamp 512 and handle 504 are in a lowered, engaged and sealed position, whereby the discharge-conduit array 500 is positioned above the receiving wells 502 such that the distal ends of the discharge conduits 510 are each directly above and within the circumference of the openings of the receiving wells 502. Thus, while the discharge-conduit array 500 is in this sealed position, a pressure differential, such as at least a partial vacuum, can be applied to the volume beneath the receiving wells 502, whereby the fluid in the distal ends of the discharge conduits 510 is urged downward through a filter medium 518. Touching-off may be disabled while the discharge-conduit array 500 is in the sealed position.

FIG. 13 shows a latch 514 that engages and secures secondary clamp 512 in the lowered and sealed position. Secondary clamp 512 can be manually released from latch 514. Handle 504 pivots about pivot point 520 allowing handle 504 to be raised and lowered. A seal replaces gaps 550 and 551 and is effected by the contact of a deformable apron 517 with the top surface 564, also referred to as deckspace 519, of platform 566. The deformable apron 517 can be compressed between components of the carriage assembly 600, or between the discharging and the receiving arrays. The deformable apron 517 can be, for example, a gasket or a suction cup-like device made of natural or silicone rubber.

Figure 14:
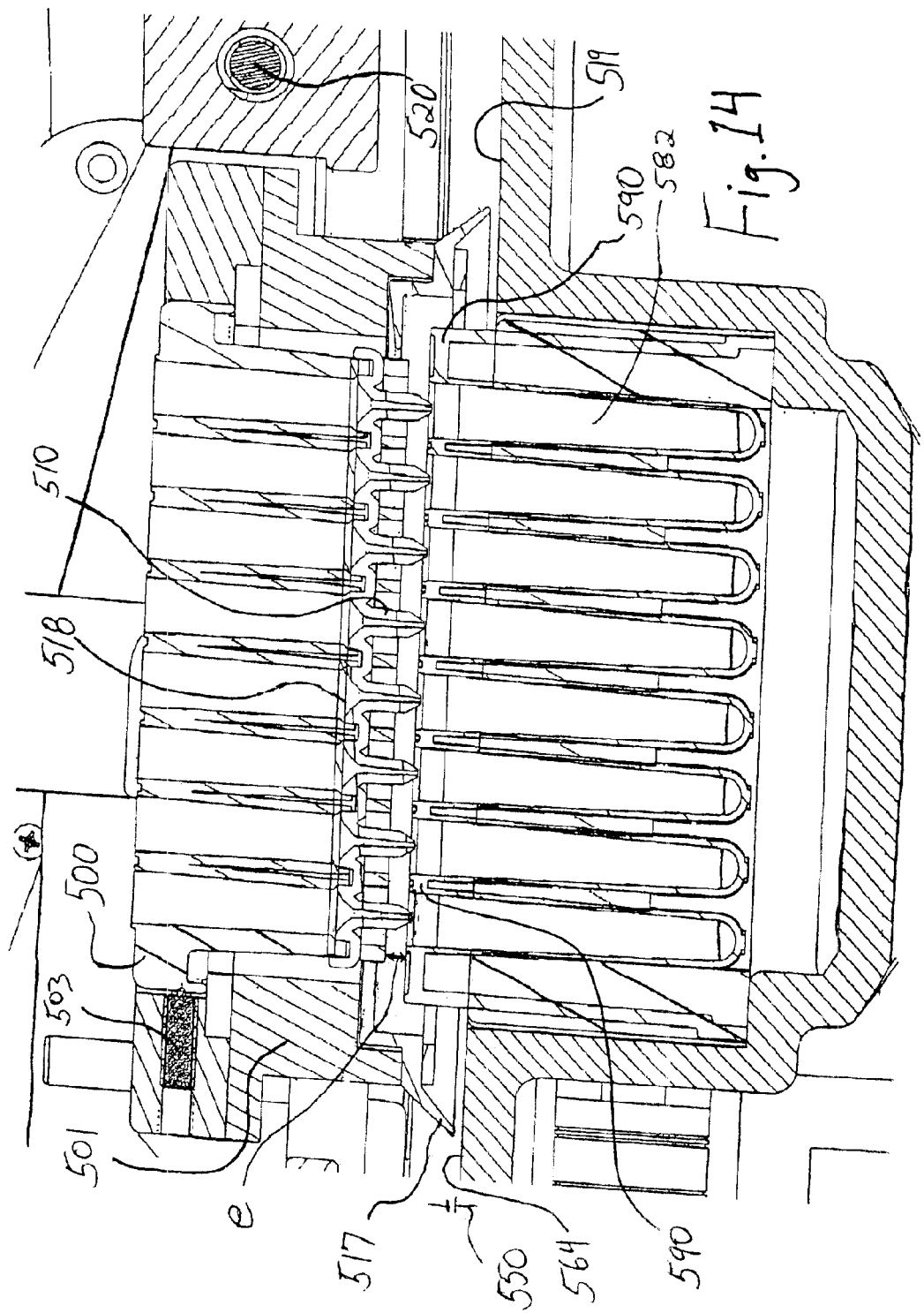
FIG. 14 is an enlarged cross-sectional view of a device according to an embodiment of the present invention showing a carriage and discharge-conduit array in a touch-off position relative to a corresponding receiving array of deep receiving wells.
Figure 15:
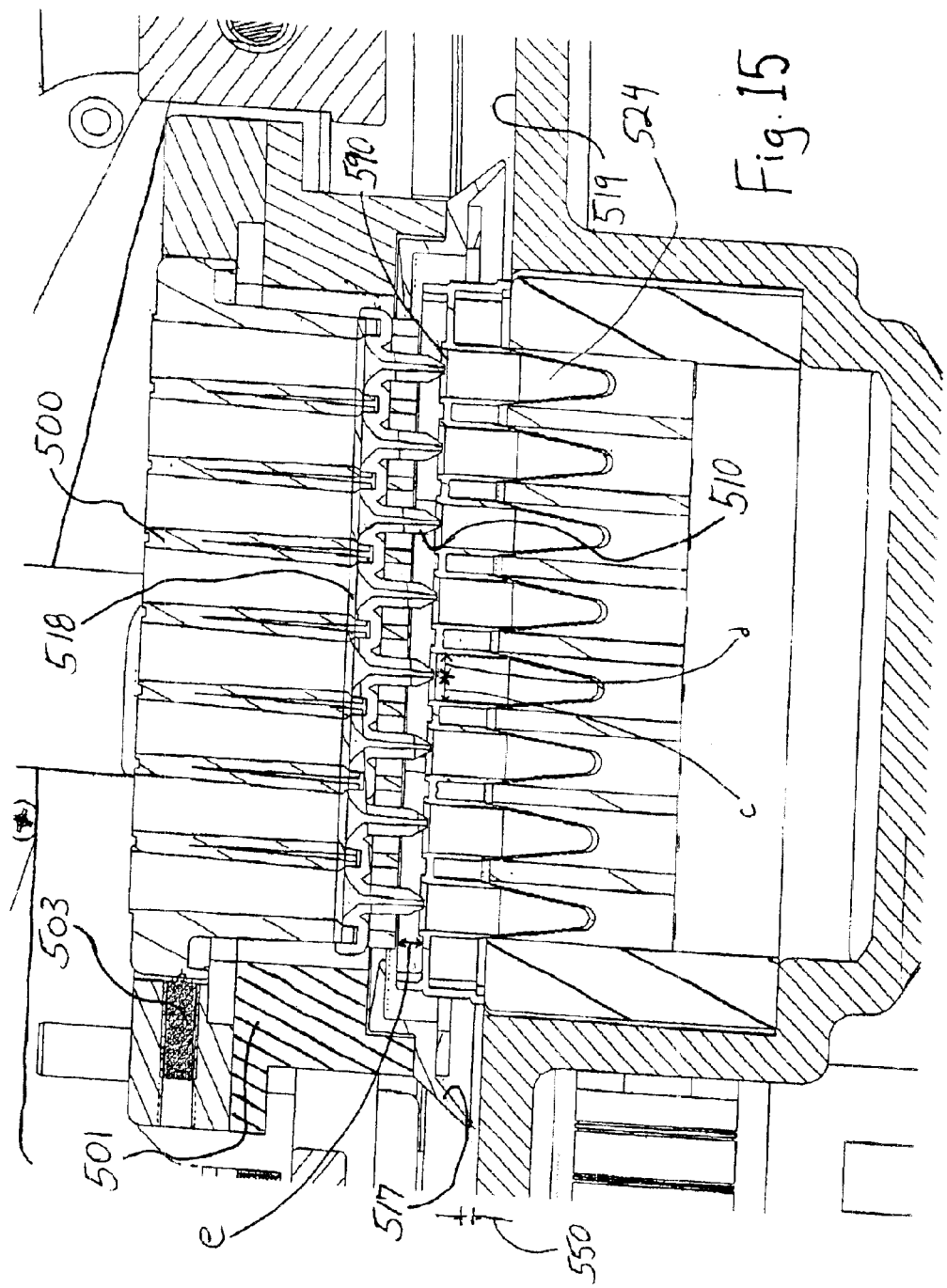
FIG. 15 is an enlarged cross-sectional view of a device according to an embodiment of the present invention showing a carriage and discharge-conduit array in a touch-off position relative to a corresponding receiving array of shallow receiving wells or microwells.

FIG. 14 is an enlarged detailed cross-sectional view of a device according to an embodiment of the present invention showing the discharge-conduit array 500 and deep receiving wells 582 in the touch-off position. A detent 503 can be provided for horizontally aligning the discharge-conduit array in the vertical positioning assembly 501. The detent 503 can include a rubber or elastomeric material. In FIG. 14, the discharge-conduit array 500 is not tightly sealed to the top of the receiving well 590, however, the distal ends of the discharge conduits 510 of the discharge-conduit array 500 are sufficiently below the top of the receiving well array 590 and able to contact the inner sidewalls of the deep receiving wells 582. A space "e" is shown between the bottom of the discharge-conduit array 500 and the top of the receiving well array 590, indicating the discharge-conduit array 500 is in the touch-off position. Filter medium 518 is positioned within each discharge conduit 510. Deep receiving wells 582 are depicted in FIG. 14, but microwells 524 can also be substituted for the deep receiving wells 582, as shown in FIG. 15. Suitable adapters can be used to adjust height requirements and size requirements of the various arrays.

Deep receiving wells can be, for example, from about 800 microliters to about 1 milliliter, and the microwells can be, for example, from about 100 to about 500 microliters.

FIG. 15 is an enlarged detailed cross-sectional view of a device according to an embodiment of the present invention showing the discharge-conduit array 500 and discharge-conduit array and shallow receiving wells 524. FIG. 15 shows a side cross-sectional view of an embodiment of a microfiltration apparatus of the present invention in the touch-off position, wherein the receiving wells are shown as microwells 524, as opposed to larger wells such as the deep receiving wells 582 shown in FIG. 14. The distal ends of the discharge conduits 510 of the discharge-conduit array 500 are positioned above the respective receiving microwells 524. FIG. 15 shows spaces "c" and "d" representing the space for linear translocation or horizontal movement of the discharge-conduit array 500 to achieve touching-off upon exerting a manual force sufficient for horizontal translocation of the discharge-conduit array 500. Manual movement of the discharge-conduit array 500 across space "d" causes the distal ends of the discharge conduits 510 to contact the inner sidewall of the microwell receiving well 524. A different manual movement of the discharge-conduit array across space "c" causes the distal ends of the discharge conduits 510 to contact the opposite inner sidewall of the microwell receiving well 524. See also FIGS. 9A, 9B, and 9C.

FIG. 16 is a front cross-sectional view of a device 499 according to an embodiment of the present invention with the discharge-conduit array 500 in the sealed position. In this representation, the discharge-conduit array 500 is positioned in a microfiltration apparatus according to an embodiment in the sealed position. In FIG. 16, the discharge-conduit array 500 is locked into an archiving, or collection station 610.

Figure 17:
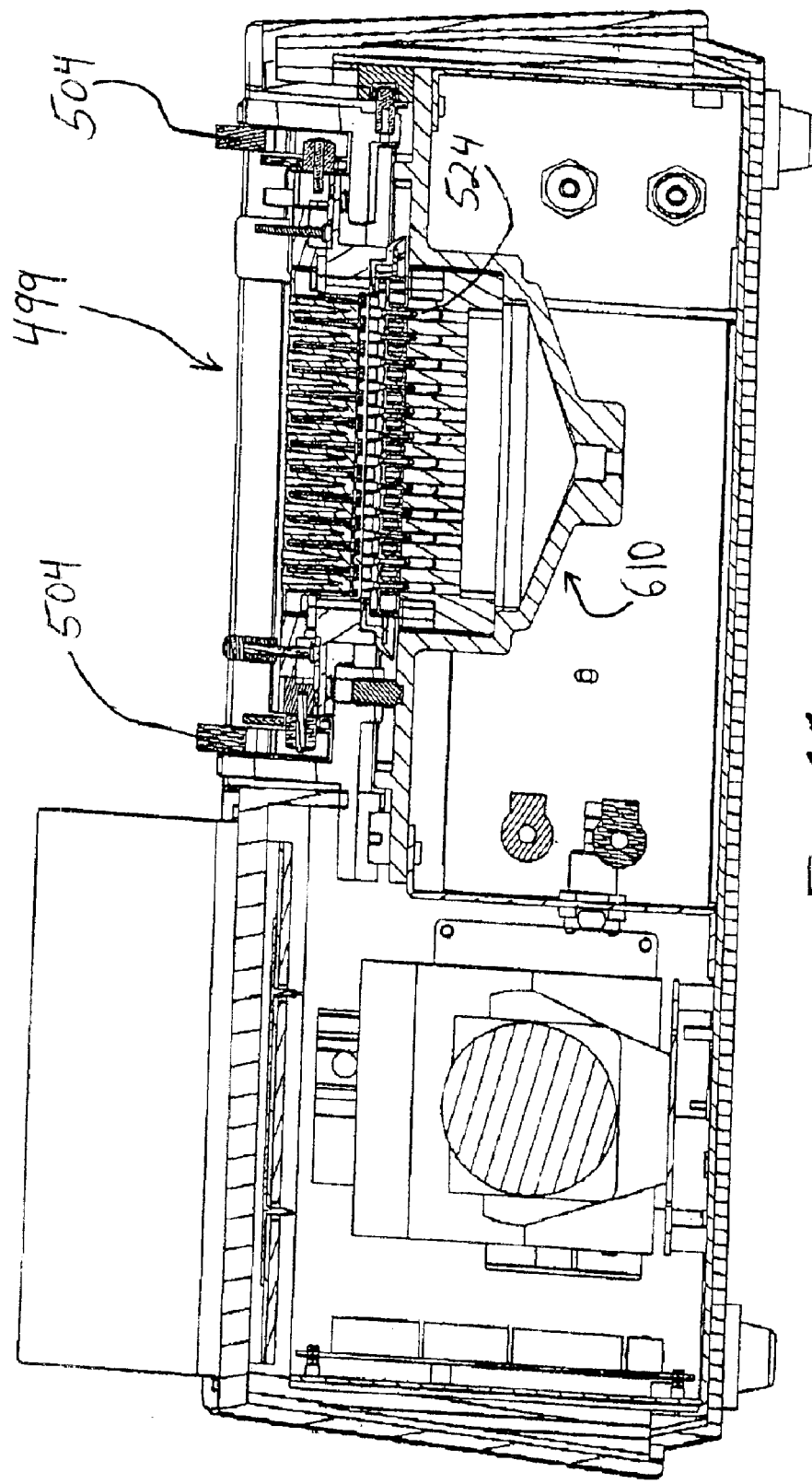
FIG. 17 is a cross-sectional front view of a device according to an embodiment of the present invention with the carriage and a shallow-well discharge-conduit array in the touch-off position.

FIG. 17 is a front cross-sectional view of a device 499 according to an embodiment of the present invention with the discharge-conduit array 500 in the touch-off position. In this representation, the discharge-conduit array 500 is in a microfiltration apparatus according to an embodiment in the touch-off position. The distal ends 570 of the discharge conduits 510 rest just within the upper openings of the corresponding receiving wells 524.

Figure 18:
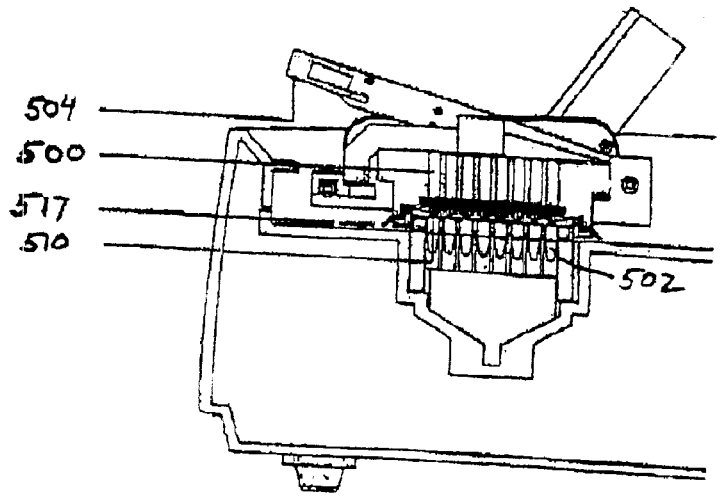
FIG. 18 is a partial cross-sectional view of a device according to an embodiment of the present invention showing the carriage and discharge-conduit array in the touch-off position and the handle in the elevated position.

FIG. 18 is a partial cross-sectional view of a device according to an embodiment of the present invention with the discharge-conduit array 500 in the touch-off position. The handle 504 is up and the seal around the deformable gasket 517, which can be, for example, a silicone gasket, has been broken. The drip directors or distal ends of the discharge conduits 510 are barely in the receiving wells 502 of the receiving or archive plate.

Figure 19:
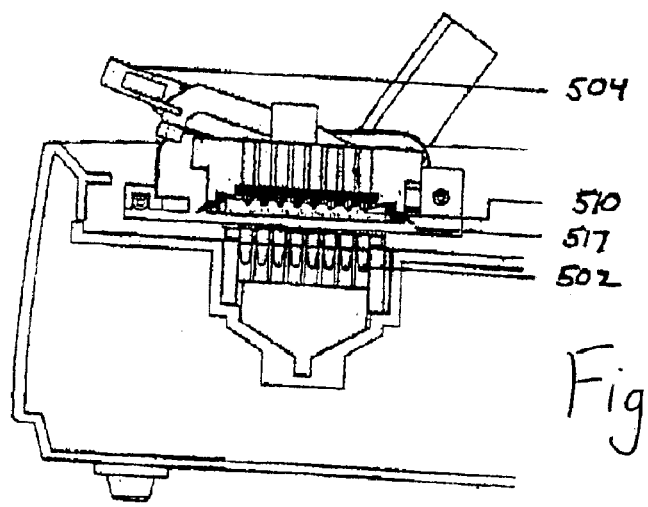
FIG. 19 is a partial cross-sectional view of a device according to an embodiment of the present invention showing the carriage and discharge-conduit array in the elevated, release, or beginning position and the handle in the beginning and release positions.

FIG. 19 is a partial cross-sectional view of a device according to an embodiment of the present invention with the discharge-conduit array 500 in the released or open position. The handle 504 is up, the drip directors or distal ends of the discharge conduits 510 are out of the receiving wells, the deformable apron 517 is lifted, and the discharge-conduit array 500 is raised and free to move to the second treatment station 612 of FIGS. 11–13.

Figure 20:
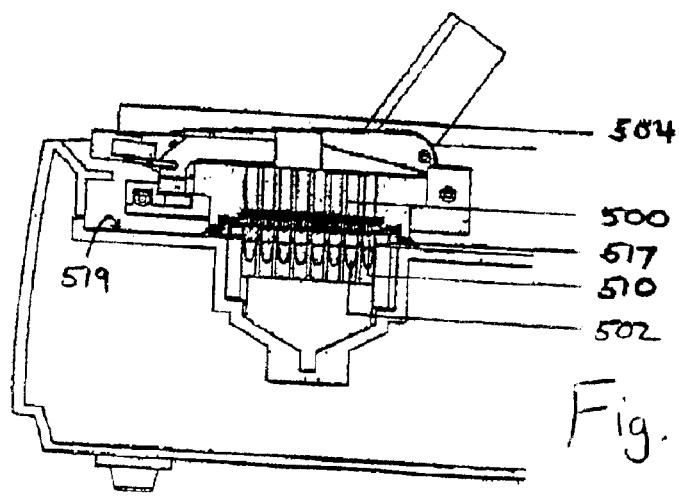
FIG. 20 is a partial cross-sectional view of a device according to an embodiment of the present invention showing the carriage and discharge-conduit array in a lowered position and the handle in a set position.

FIG. 20 is a partial cross-sectional view of a device according to an embodiment of the present invention with the discharge-conduit array 500 in the sealed or closed position. The handle 504 is down and locked, the discharge-conduit array 500 is positioned over the receiving wells, the deformable apron 517 is in contact with the deckspace 519 or top surface 564 of the platform 566 to form a seal therewith, and the distal ends of the discharge conduits 510 are within the openings of the receiving wells 502.

FIG. 21 is a perspective view of a device according to an embodiment of the present invention with the discharge-conduit array 500 in the touch-off position. The handle 504 is up, and release mechanism 505 located in the handle 504 can be manually compressed against a biasing means 507 (not seen in FIG. 21). Secondary clamp 512 is engaged with latch 514. The carriage assembly is provided with one or more retaining device or pivotable detent 640 to secure the discharge-conduit array to the carriage assembly 600. A release lever 609 is provided for releasing the latch 514 from the secondary clamp 512. FIG. 21 also shows the pivotable detent 640 vertically locking the discharge-conduit array in the vertical positioning assembly 501 shown in FIGS. 14 and 15.

FIG. 22 is a perspective view of a device according to an embodiment of the present invention with the discharge-conduit array 500 in the released or open position. The handle 504 is up, and the secondary clamp 512 is released from the latch 514.

FIG. 23 is a perspective view of a device according to an embodiment of the present invention with the discharge-conduit array 500 in the sealed or closed position. The handle 504 is fully depressed, and the discharge-conduit array 500 is positioned over the receiving well tray.

FIG. 24a is a partial cross-sectional view of a device according to an embodiment of the present invention with the discharge-conduit array 500 in the touch-off position. The handle 504 is up, the deformable apron 517 is not in contact with the deckspace 519 or top surface 564, and a gap 550 is provided between the deformable apron 517 and deckspace 519. The distal ends 570 of the discharge conduits 510 are just inside the openings of the receiving wells 502, and pendent drops are able to touch-off to the inner sidewalls of said receiving wells 502 upon the application of a sufficient manual horizontal force applied to the discharge-conduit array 500 via the handle 504.

FIG. 24b is a partial cross-sectional view, reverse view to FIG. 24a, of a device according to an embodiment of the present invention with the discharge-conduit array 500 in the touch-off position.

Figure 25:
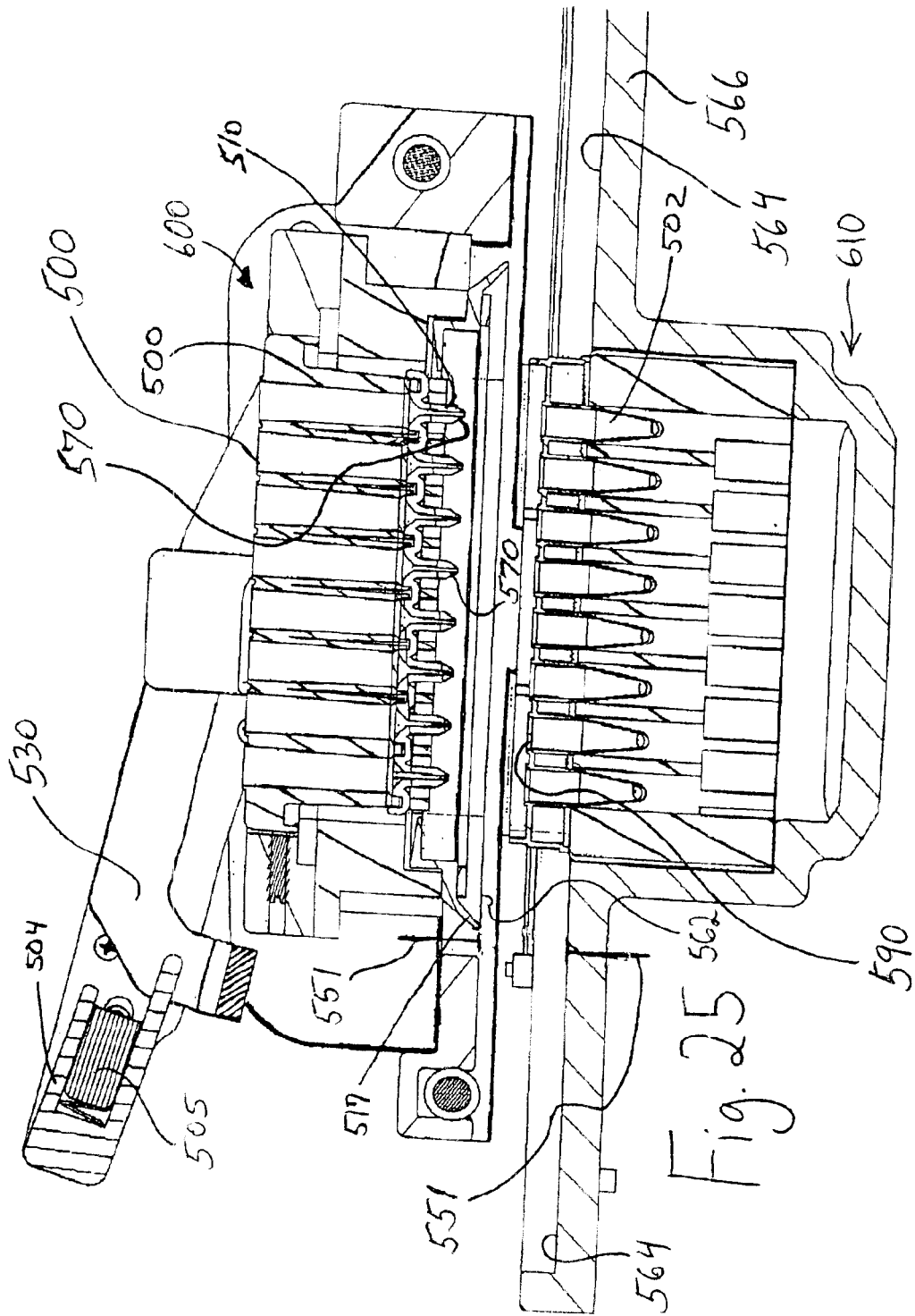
FIG. 25 is a partial cross-sectional view of a device according to an embodiment of the present invention showing the carriage and discharge-conduit array in the elevated, beginning, or release position and the handle in the beginning or release position.

FIG. 25 is a partial cross-sectional view of a device according to an embodiment of the present invention with the discharge-conduit array 500 in the released or open position. The handle 504 is up, the drip directors or distal ends of the discharge conduits 510 are out of the receiving wells 502, the deformable apron 517 is lifted, and the discharge-conduit array 500 is raised and free to move to second treatment station 612 shown in FIGS. 11–13.

FIG. 26 is a partial cross-sectional view of a device according to an embodiment of the present invention with the discharge-conduit array 500 in the sealed or closed position. The handle 504 is down and locked, the discharge-conduit array 500 is positioned over the receiving wells 502, the deformable apron 517 is in contact with the deckspace 519 or top surface 564 of platform 566 to form a seal therewith, and the distal ends of the discharge conduits 510 are within the upper openings of the receiving wells 502.

FIG. 27 is a partial side view of a device according to an embodiment of the present invention with the discharge-conduit array 500 and carriage, and the handle, in the touch-off positions. The arm 642 is guided in movement by a sleeve 643.

In various embodiments of the apparatus of the present invention, the apparatus is equipped with the second treatment station 612. Station 612 can be used, for example, to transfer waste washed from the discharge-conduit array station to a waste receptacle. Station 612 can be provided with a splash guard plate to prevent cross-contamination between receiving wells. When the discharge-conduit array 500 is located at station 612, touch-off can be performed, as well as the application of pressure differentials, such as vacuum operations, separately, or simultaneously.

The manual translocation or horizontal movement of the carriage assembly 600, and discharge-conduit array 500, according to the present invention does not need to be a large distance for touch-off. The translocation need only be sufficient to facilitate the touching-off of the pendent drops from the distal ends of the discharge conduits into the respective receiving wells. Thus, the translocation need only be a distance approximately equal to or less than, but no greater than, the diameter of the opening of the receiving well into which the distal ends of the discharge conduits is extended. This can be in an embodiment, for example, and not as a limitation herein, a distance of from about one-sixteenth of an inch up to about one and a half inches. The translocation distance useful in the touching-off operation of the present invention is illustrated as spaces "c" and "d" in FIG. 15.

According to various embodiments of the present invention, the discharge-conduit array can include selected elements shown in FIG. 2. Thus, for example, and not by limitation herein, a useful discharge-conduit array according to an embodiment can include elements numbered 40, 8 and 14 to form a purification tray of discharge conduits with drip directors, wherein the purification tray can be manually translocated to achieve touching-off of the distal ends of the drip directors to the inner sidewalls of the receiving wells. Other elements for incorporation into a discharge-conduit array adapted for manual translocation for improved touching-off will be recognized by those skilled in the art from the elements described and shown in FIG. 2.

The present invention also provides, according to various embodiments, a method of purifying a sample in a microfiltration apparatus having an array of a plurality of discharge conduits each of which contains a filtration medium. The conduits are positioned above an array of a plurality of corresponding receiving wells having inner sidewalls. The method includes: providing a fluid sample into the discharge conduits; passing the sample through the filtration medium to produce a filtrate; and manually shifting in a generally horizontal direction the array of discharge conduits, whereby the shifting causes pendent drops of fluid hanging from the discharge conduits to contact the inner sidewalls of the receiving wells. Various embodiments of the methods of the present invention can also be understood with reference to the above description of the apparatus.

Those skilled in the art can now appreciate from the foregoing description that the broad teachings of the present invention can be implemented in a variety of forms. Therefore, while this invention has been described in connection with particular embodiments and examples thereof, the true scope of the invention should not be so limited. Various changes and modification may be made without departing from the scope of the invention, as defined by the appended claims.

What is claimed is:

1. An apparatus, comprising:
   (i) a carriage configured to carry a first array and adapted for movement along a first, generally horizontal, axis from and to a neutral position whereat the first array and a corresponding second array are substantially axially aligned, wherein the first array is one of a discharge-conduit array and a receiving array, and the second array is the other of a discharge-conduit array and a receiving array, and wherein the discharge conduit array comprises discharge conduits and the receiving array comprises receiving wells or receiving holes;
   (ii) a vertical positioning assembly configured for supporting the first array for movement along a second, generally vertical, axis between (a) a first position whereat the discharge conduits of the discharge conduit array clear the receiving wells or receiving holes of the receiving array, (b) a second position whereat the discharge conduits extend down into the receiving wells or receiving holes of the corresponding receiving array, and (c) a touch-off position intermediate the first and second positions whereat pendent drops hanging from the discharge conduits contact respective inner sidewalls of respective receiving wells or receiving holes of the receiving array upon the movement of the carriage along the first axis; and
   (iii) a manually-operable handle connected to the carriage and the vertical positioning assembly and configured such that a movement of the handle moves the carriage along the first axis, and a second movement of handle moves the vertical positioning assembly along the second axis.

2. The apparatus of claim 1, wherein the first array is the discharge-conduit array, and the second array is the receiving array.

3. The apparatus of claim 1, wherein the handle is configured for pivotal movement from a beginning position to a set position, from the set position to an intermediate position, and from the intermediate position to a release position.

4. The apparatus of claim 3, wherein the handle includes two or more levers.

5. The apparatus of claim 3, wherein the beginning position is an elevated position, the set position is a depressed position, and the intermediate position is intermediate the beginning position and the set position.

6. The apparatus of claim 5, wherein the release position is the same as the beginning position.

7. The apparatus of claim 5, wherein the carriage is connected to the handle such that: when the handle is in the elevated beginning position, the vertical positioning assembly is in the elevated position; when the handle is in the set position, the vertical positioning assembly is in the lowered position; and when the handle is in the intermediate position, the vertical positioning assembly is in the touch-off position.

8. The apparatus of claim 5, further including a releasable lock wherein when the handle is depressed into the set position, the releasable lock is adapted to activate and maintain the vertical positioning assembly in the set position until the lock is released.

9. The apparatus of claim 1, further comprising a vacuum system for drawing a vacuum through the discharge-conduit array when the carriage is in the second position.

10. The apparatus of claim 1, wherein the first position is an elevated position and the second position is a lowered position.

11. An apparatus, comprising:
   a platform having a first treatment station and a second treatment station, each of the treatment stations including a holder for securing a receiving array of receiving wells or receiving holes;
   a carriage configured to carry a discharge-conduit array into a position above a first receiving array of receiving wells or receiving holes at the first treatment station, and configured to carry the discharge-conduit array into a position above a corresponding second receiving array of receiving wells or receiving holes at the second treatment station, the carriage being configured for: (1) movement between the first treatment station and the second treatment station; (2) movement at the first treatment station along a first, generally horizontal, axis from a neutral position whereat the discharge-conduit array and the first receiving array are substantially axially aligned; and (3) second movement at the second treatment station along a second, generally horizontal, axis from a neutral position whereat the discharge-conduit may and the second receiving array are substantially axially aligned;
   a vertical positioning assembly for supporting the discharge-conduit array for linear movement at the first treatment station along a third, generally vertical, axis between (a) an elevated position whereat the discharge conduits clear the receiving wells or receiving holes of the first receiving array, (b) a lowered position whereat the discharge conduits extend down into respective receiving wells or receiving holes of the first receiving array, and (c) a touch-off position intermediate the elevated and lowered positions whereat pendent drops banging from the discharge conduits contact respective sidewalls of respective ones of the receiving wells or receiving holes of the first receiving array upon the movement of the carriage along the first axis; and a manually operable handle connected to the carriage and the vertical positioning assembly such that a movement of the handle at the first treatment station moves the carriage along the first axis, a second movement of the handle at the second treatment station moves the carriage along the second axis, and a third movement of the handle moves the vertical positioning assembly along at least the third axis.

12. The apparatus of claim 11, wherein the handle is configured for pivotal movement at the first treatment station from a beginning position to a set position, from the set position to an intermediate position, and from the intermediate position to a release position.

13. The apparatus of claim 12, wherein the beginning position is an elevated position, the set position is a depressed position, and the intermediate position is intermediate the beginning position and the set position.

14. The apparatus of claim 13, wherein the handle is connected to the carriage such that movement of the handle to the release position translates into movement of the carriage into a transfer position whereat the carriage can be moved horizontally from the first treatment station to the second treatment station.

15. The apparatus of claim 14, wherein a carriage guide track is provided on the platform for guiding the carriage through a predetermined path from the first treatment station to the second treatment station.

16. The apparatus of claim 11, wherein the first treatment station is a sample wash station, and the second treatment station is a sample collection station.

17. The apparatus of claim 11, wherein the vertical positioning assembly supports the discharge-conduit array for movement at the second treatment station along a fourth, generally vertical, axis between (d) an elevated position whereat the discharge conduits clear the receiving wells or receiving holes of the second receiving array, (e) a lowered position whereat the discharge conduits extend down into respective receiving wells or receiving holes of a second receiving array, and (f) a touch-off position intermediate the elevated and lowered positions whereat pendent drops hanging from the discharge conduits contact respective sidewalls of respective ones of the receiving wells or receiving holes of the second receiving array upon the second movement of the carriage along the second axis.

18. The apparatus of claim 17, wherein the handle is connected to the carriage and the vertical positioning assembly such that when the carriage is at the second treatment station movement of the handle translates into the movement of the vertical positioning assembly along the fourth axis.

19. The apparatus of claim 17, further including a releasable lock wherein when the handle is depressed into the set position in the first treatment station, in the second treatment station, or in both the first treatment station and the second treatment station, the releasable lock is adapted to activate and maintain the vertical positioning assembly in the set position until the lock is released.

20. A method, comprising:

providing a carriage configured to carry one of a discharge-conduit array and a corresponding receiving array;

providing a vertical positioning assembly supporting one of the discharge-conduit array and the receiving array at a touch-off position whereat pendent drops of liquid hanging from discharge conduits disposed in the discharge-conduit array contact respective sidewalls of respective ones of receiving wells or receiving holes of the corresponding receiving array upon movement of one or more of the discharge-conduit array and the receiving array, along a substantially horizontal axis;

providing a manually-operable handle connected to the carriage and the vertical positioning assembly such that a movement of the handle moves the carriage along the substantially horizontal axis; and touching-off in a substantially simultaneous fashion, pendent drops of fluid hanging from the discharge conduits of the discharge-conduit array to inner sidewalls of respective receiving wells or receiving holes of the corresponding receiving array, wherein the touching-off is effected by shifting the carriage to cause the movement along the substantially horizontal axis of at least one of the discharge-conduit array and the receiving array from a beginning position to a touch-off position whereat the pendent drops contact the respective sidewalls of the respective receiving wells or receiving holes.

21. The method of claim 20, wherein the touching-off further comprises shifting the discharge conduits into contact with respective sidewall portions of respective receiving wells or receiving holes of the corresponding receiving array, and then shifting each of the discharge conduits into contact with laterally opposing, sidewall portions of the same respective receiving wells or receiving holes.

22. The method of claim 21, wherein the touching-off consists of a shifting the discharge conduits of the discharge-conduit array into contact with a first sidewall portion of a respective receiving well or receiving hole, one time, and shifting the discharge conduits into contact with a respective opposing sidewall portion of the respective receiving well or receiving hole, one time.

23. The method of claim 20, further comprising moving the handle in a pivotal movement to effect vertical movement of the carriage, from a beginning position to a set position, from the set position to an intermediate position, and from the intermediate position to a release position.

24. The method of claim 23, wherein the beginning position is an elevated position, the set position is a depressed position, and the intermediate position is intermediate the beginning position and the set position.

25. The method of claim 24, wherein the release position is the same as the beginning position.

26. The method of claim 23, wherein the vertical positioning assembly supports the carriage for movement vertically between an elevated position, a lowered position, and the touch-off position, and the method further comprises drawing a vacuum through the discharge-conduit array when the carriage is in the lowered position.

27. The method of claim 26, wherein the carriage is connected to the handle such that: when the handle is in the beginning position, the vertical positioning assembly is in the elevated position; when the handle is in the set position, the vertical positioning assembly is in the lowered position; and when the handle is in the intermediate position, the vertical positioning assembly is in the touch-off position.

28. The method of claim 26, further comprising activating a releasable lock when the handle is in the set position, to maintain the vertical positioning assembly and the carriage in the lowered position until the lock is released.

29. The method of claim 20, wherein the carriage carries the discharge-conduit array.

30. The method of claim 29, further comprising moving the carriage to a second treatment station whereat the discharge conduits of the discharge-conduit array are substantially axially aligned with respective receiving wells or receiving holes of a second corresponding receiving array.

31. A method, comprising:
providing a platform having a first treatment station and a second treatment station, the first treatment station including a first holder for securing a first receiving array of receiving wells or receiving holes, and the second treatment station including a second holder for securing a second receiving array of receiving wells or receiving holes;
providing a carriage configured to carry a discharge-conduit array into a position above a first receiving array of receiving wells or receiving boles at the first treatment station, and configured to carry the discharge-conduit array into a position above a corresponding second receiving array of receiving wells or receiving boles at the second treatment station, the carriage being adapted for (1) movement between the first treatment station and the second treatment station; (2) movement at the first treatment station along a first, generally horizontal, axis from and to a neutral position whereat discharge conduits of the discharge-conduit array and receiving wells or receiving holes of the first receiving array are substantially axially aligned; and (3) second movement at the second treatment station along a second, generally horizontal, axis from and to a neutral position whereat discharge conduits of the discharge-conduit array and receiving wells or receiving holes of the second receiving array are substantially axially aligned;
providing a vertical positioning assembly for supporting the discharge-conduit array for movement at the first treatment station along a third, generally vertical, axis between (a) an elevated position whereat the discharge conduits clear the receiving wells or receiving holes of the first receiving array, (b) a lowered position whereat the discharge conduits extend down into respective receiving wells or receiving holes of the first receiving array, and (c) a touch-off position intermediate the elevated and lowered positions whereat pendent drops hanging from the discharge conduits contact respective sidewalls of respective receiving wells or receiving holes of the first receiving array upon movement of the carriage along the first axis;
providing a manually-operable handle connected to the carriage and the vertical positioning assembly such that a movement of the handle at the first treatment station moves the carriage along the first axis, a second movement of the handle at the second treatment station moves the carriage along the second axis, and a third movement of the handle moves the vertical positioning assembly along the third axis; and
with the carriage positioned at the first treatment station, touching-off in a substantially simultaneous fashion, the pendent drops of fluid hanging from the discharge conduits to inner sidewalls of respective receiving wells or receiving holes of the first receiving array, wherein the touching-off is effected by shifting the carriage to cause the movement of the carriage along the first axis while the first receiving array is maintained in a substantially fixed position.

32. The method of claim 31, wherein the touching-off further comprises shifting the discharge conduits into contact with sidewall portions of respective receiving wells or receiving holes of the first receiving array, and then shifting the discharge conduits into contact with laterally opposing, sidewall portions of the same respective receiving wells or receiving holes of the first receiving array.

33. The method of claim 31, further comprising moving the handle in a pivotal movement at the first treatment station from a beginning position to a set position, from the set position to an intermediate position, and from the intermediate position to a release position.

34. The method of claim 33, wherein the beginning position is an elevated position, the set position is a depressed position, and the intermediate position is intermediate the beginning position and the set position.

35. The method of claim 34, wherein the handle is connected to the carriage such that movement of the handle to the release position translates into movement of the carriage into the elevated position whereat the carriage can be moved horizontally from the first treatment station to the second treatment station, and the method further comprises moving the carriage from the first treatment station to the second treatment station.

36. The method of claim 35, wherein samples in the discharge-conduit array are washed at the first treatment station and the samples are collected at the second treatment station.

37. The method of claim 31, wherein the vertical positioning assembly supports the discharge-conduit array for movement at the second treatment station along a fourth, generally vertical, axis between (d) an elevated position whereat the discharge conduits of the discharge-conduit array clear the receiving wells or receiving holes of the second receiving array, (e) a lowered position whereat the discharge conduits extend down into respective receiving wells or receiving holes of the second receiving array, and (f) a touch-off position intermediate the elevated and lowered positions whereat pendent drops hanging from the discharge conduits contact respective sidewalls of respective receiving wells or receiving holes of the second receiving array upon the second movement of the carriage along the second axis; and
the method further comprises positioning the carriage at the second treatment station and touching-off, in a substantially simultaneous fashion, the pendent drops of fluid hanging from the discharge conduits to inner sidewalls of respective receiving wells or receiving holes of the second receiving array, wherein the touching-off is effected by shifting the carriage along the second axis to cause the second movement of the discharge-conduit array while the second receiving array is maintained in a substantially fixed position.

38. The method of claim 37, wherein the touching-off further comprises shifting each of the discharge conduits into contact with one sidewall portion of respective receiving wells or receiving holes of the second receiving array, and then shifting the discharge conduits into contact with laterally opposing, sidewall portions of the same respective receiving wells or receiving holes of the second receiving array.

39. The method of claim 37, further comprising activating a releasably lock when the handle is depressed into the set position in the first treatment station to maintain the vertical positioning assembly and carriage in the lowered position until the lock is released.

* * * * *

UNITED STATES PATENT AND TRADEMARK OFFICE
CERTIFICATE OF CORRECTION

PATENT NO. : 6,896,849 B2
DATED : May 24, 2005
INVENTOR(S) : Reed et al.

It is certified that error appears in the above-identified patent and that said Letters Patent is hereby corrected as shown below:

Column 31,
Line 47, delete "and";
Line 54, change "and wherein" to -- wherein --;

Column 32,
Line 7, change "of handle" to -- of the handle --;
Line 64, change "may" to -- array --; and Column 33,
Line 9, change "banging" to -- hanging --.

Signed and Sealed this

Sixth Day of June, 2006

JON W. DUDAS
*Director of the United States Patent and Trademark Office*